United States Patent [19]

Harada et al.

[11] Patent Number: 4,721,564
[45] Date of Patent: Jan. 26, 1988

[54] APPARATUS FOR THE FILTRATION OF PLASMA FROM BLOOD

[75] Inventors: Yoshimichi Harada; Akiyoshi Nakano; Takuichiro Watanabe, all of Okayama, Japan

[73] Assignees: Kuraray Co., Ltd., Okayama; Kawasumi Laboratories Inc., Tokyo, both of Japan

[21] Appl. No.: 919,127

[22] Filed: Oct. 15, 1986

[30] Foreign Application Priority Data

Oct. 22, 1985 [JP] Japan .................................. 60-236205
Nov. 20, 1985 [JP] Japan .................................. 60-262108

[51] Int. Cl.$^4$ .............................................. B01D 13/00
[52] U.S. Cl. ..................................... 210/88; 210/433.2
[58] Field of Search ..................... 604/4, 5, 6; 210/88, 210/195.2, 416.1, 433.2, 641

[56] References Cited

U.S. PATENT DOCUMENTS

| | | | |
|---|---|---|---|
| 4,350,594 | 9/1982 | Kawai et al. | 210/637 |
| 4,397,747 | 8/1983 | Ikeda | 210/641 |
| 4,416,772 | 11/1983 | Sato et al. | 210/137 |
| 4,492,531 | 1/1985 | Kenji et al. | 417/279 |
| 4,547,289 | 10/1985 | Okano et al. | 210/652 |
| 4,605,503 | 8/1986 | Bilstap et al. | 210/433.2 X |
| 4,648,866 | 3/1987 | Malbrancq et al. | 210/195.2 X |

*Primary Examiner*—Frank Spear
*Attorney, Agent, or Firm*—Kramer, Brufsky & Cifelli

[57] ABSTRACT

A blood processing apparatus which comprises a blood circulating circuit including a plasma filter, a plasma circulating circuit for draining at least a portion of the blood plasma and for supplying a physiologically compatible fluid substitute to the subject through a portion of the blood circulating circuit, a blood pump and a drain pump, a priming fluid source adapted to be connected with the blood outlet and a fluid substitute inlet, a first detector for detecting the flow through the blood circulating circuit, a second detector for detecting the flow through the plasma circulating circuit, a first valve for selectively establishing and interrupting a first fluid circuit between a downstream portion of the plasma circulating circuit adjacent the blood outlet and that portion of the blood circulating circuit downstream of the plasma filter, a second valve for selectively establishing and interrupting a second fluid circuit between the downstream portion of the plasma circulating circuit and the outside of the apparatus, a blood pump drive for driving the blood pump to cause the priming fluid to flow through the blood circulating circuit, and a drain pump drive operable in response to an output signal from the first detector for driving the drain pump to cause the priming fluid to flow through the blood circulating circuit when the flow through the blood circulating circuit attains a first predetermined value.

5 Claims, 29 Drawing Figures

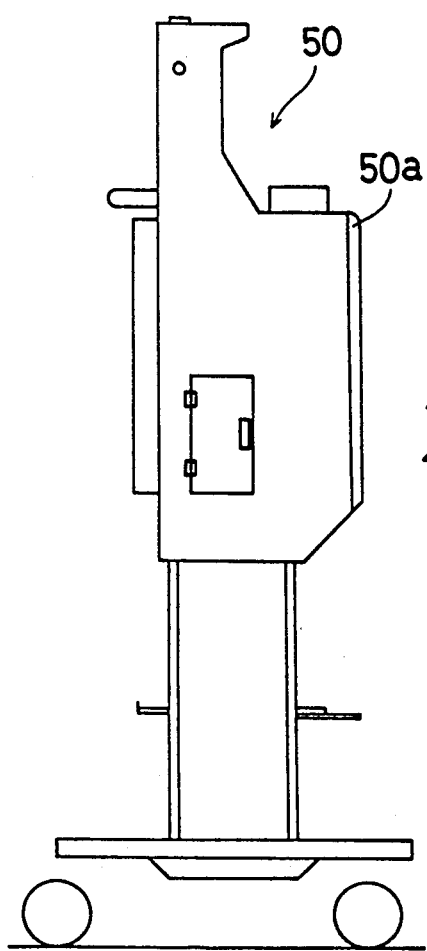
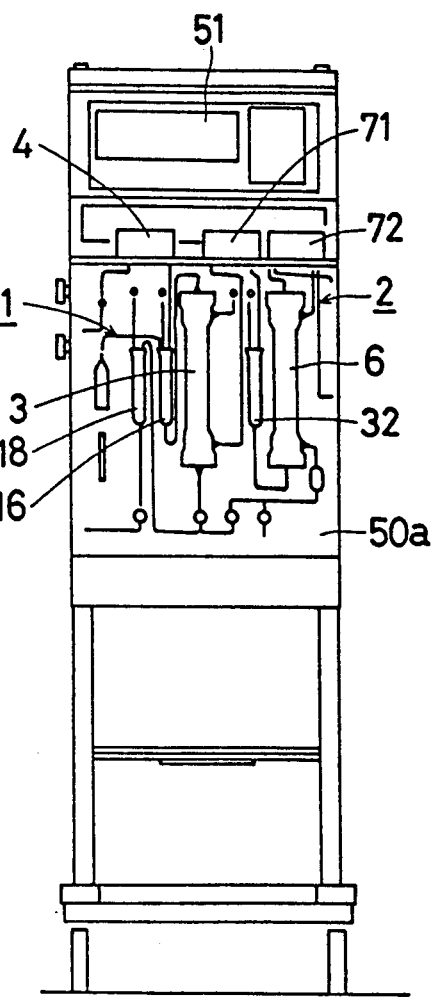

Fig. 6 (Mode S1)

Fig. 7 (Mode S2)

Fig. 8 (Mode S3)

Fig. 9 (Mode S4)

Fig. 10 (Mode S5)

Fig. 11 (Mode S6)

Fig. 13 (Mode S8)

Fig. 14
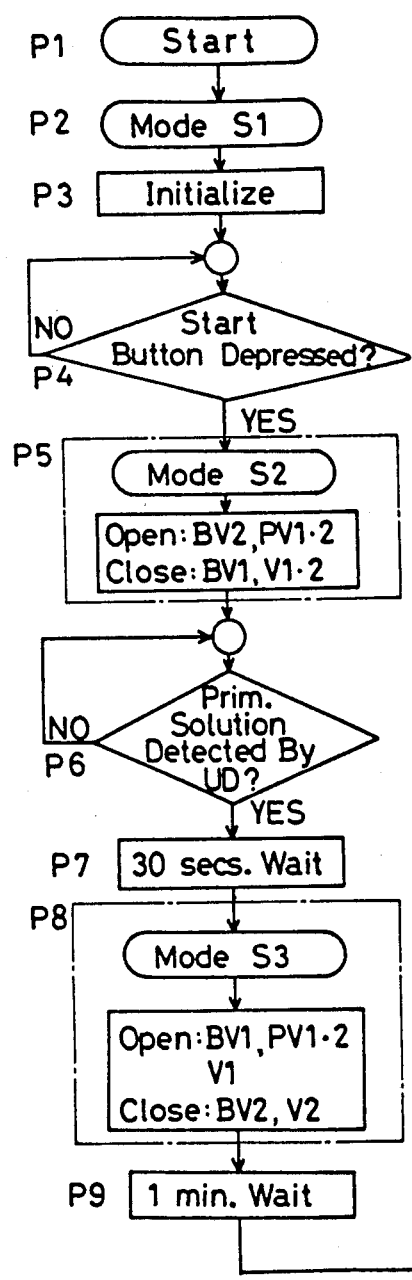
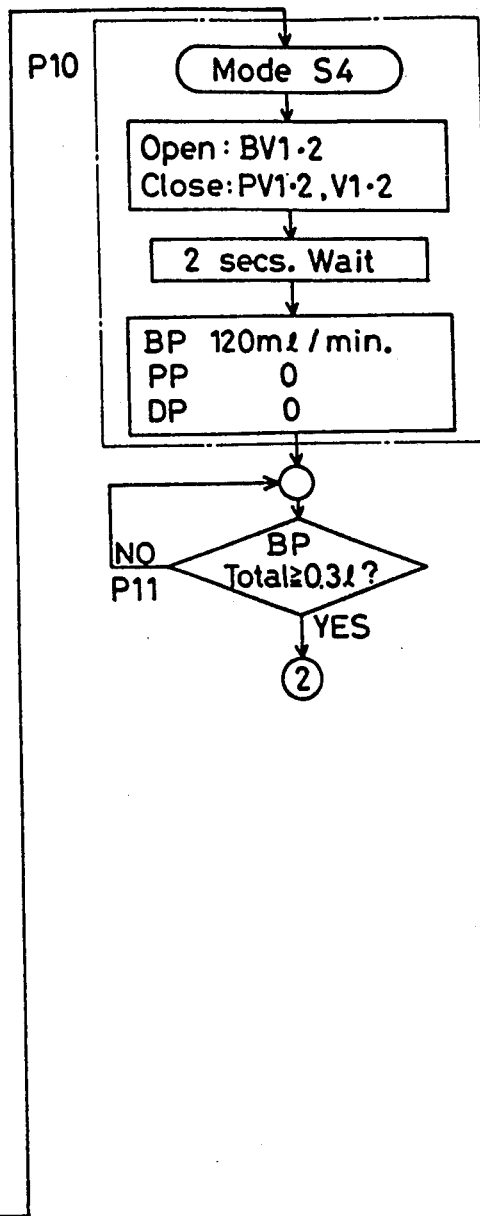

Fig. 22 (Mode M1)

Fig. 23 (Mode M2)

Fig. 24 (Mode M3)

Fig. 26 (Mode M5)

Fig. 27 (Mode M6)

APPARATUS FOR THE FILTRATION OF PLASMA FROM BLOOD

BACKGROUND OF THE INVENTION

1. Field of Technology

The present invention generally relates to an apparatus for separating blood plasma and blood corpuscles from whole blood and, more particular, to the apparatus designed to be automatically primed.

In particular, the plasma filtration apparatus to which the present invention pertains comprises at least one plasma separator or filter for removing plasma from whole blood pumped from a patient, either human or animal, the remainder of the whole blood being subsequently returned to the patient after having been supplemented with an amount of physiologically compatible fluid substitute equal to the amount of the removed plasma.

2. (Description of the Prior Art)

Methods for treating a patient suffereing from kidney or liver failure or auto-immunization or the like disease are known. One such system employs a plasma separation method as well as an apparatus capable of performing the plasma separation wherein the whole blood extracted from the patient's artery is separated by a plasma separator or filter into blood plasma and blood corpuscles. The separated blood corpuscles are then returned to the patient's veins together with a physiologically compatible fluid substitute in a quantity sufficient to compensate for the reduction of the removed plasma.

According to the Japanese Laid-open Patent Publication No. 60-40302, there is disclosed the use of an additional plasma separator or filter for separating the blood plasma, which has been previously separated from the blood corpuscles in the manner as hereinabove described into a high molecular component containing various toxic substances and a low molecular component containing substances, such as, protein, useful to metabolism. In this case, the lower molecular component is returned to the patient together with the physiologically compatible fluid substitute in a quantity sufficient to compensate for the reduction of the removed high molecular component.

When using any of these prior art blood processing apparatuses thereof prior to the whole blood being processed during the clinical operation, the entire fluid circuit employed in the blood processing apparatus must be primed with physiological sodium chloride solution (normal saline solution) in order for the entire fluid circuit to be cleansed and to be rendered adaptable for the whole blood to be processed.

Hitherto, the priming procedure was carried out by disconnecting the plasma separator or separators from the fluid circuit and, after the disconnected plasma separator or separators were primed, connecting them to the fluid circuit components to complete the entire fluid circuit profile. Therefore, the priming procedure hitherto carried out was complicated and time-consuming, requiring the attendance of one or more skilled technicians. This was particularly true where two plasma separators or filters was employed such as in the apparatus disclosed in the above mentioned Japanese publication.

SUMMARY OF THE INVENTION

The present invention has been developed with an aim of substantially eliminating the above discussed problems inherent in the prior art blood processing apparatuses and has for its essential object to provide an improved blood processing apparatus which does not require the temporary removal of the plasma separator or separators from the remaining fluid circuit preparatory to the priming operation.

It is another, but important object of the present invention to provide an improved blood processing apparatus of the type referred to above, wherein the priming can be automatically executed with no need to remove the plasma separator or separator from the fluid ciruit.

In order to accomplish these objects of the present invention, there is provided a plasma filtration apparatus which comprises a blood circulating circuit means including a plasma filter for separating whole blood, extracted from a subject of interest through a blood inlet, into a blood plasma component and a blood corpuscle component and for supplying the blood corpuscle component to a blood outlet for the return thereof to the subject of interest, and a plasma circulating circuit means for draining at least a portion of the blood plasma component, which has been separated from the whole blood, and for supplying a physiologically compatible fluid substitute in a quantity substantially equal to the amount of said portion of the blood plasma component, which has been drained, to a portion of the blood circulating circuit means downstream of the plasma filter and then to the blood outlet.

The apparatus further comprises a first pumping means disposed on the blood circulating circuit means, a second pumping means disposed on the plasma circulating circuit means, a source of priming fluid adapted to be fluid-connected with the blood inlet and that portion of the plasma circulating circuit means through which the fluid substitute is introduced into the plasma circulating circuit means, a first detector for detecting the flow through the blood circulating circuit means, a second detector for detecting the flow through the plasma circulating circuit means, a first valving means for selectively establishing and interrupting a first fluid circuit between a downstream portion of the plasma circulating circuit means adjacent the blood outlet and said portion of the blood circulating circuit means downstream of the plasma filter, and a second valving means for selectively establishing and interrupting a second fluid circuit between said portion of the plasma circulating circuit means adjacent the blood outlet and the outside of the apparatus.

The apparatus further comprises a first drive means operable to cause the first and second valving means to interrupt the respective first and second fluid circuits and for driving the first pumping means to cause the priming fluid to flow through the blood circulating circuit means, a second drive means operable in response to an output signal from the first detector for causing the second valving means to establish the second fluid circuit and, at the same time, driving the second pumping means to cause the priming fluid to flow through the plasma circulating circuit means when the flow through the blood circulating circuit means attains a first predetermined value, and means operable in response to respective output signals from the first and second detectors for bringing the first and second pumping means to a halt when both of the flows through the blood circulating circuit means and the plasma circulating circuit means attain a second predetermined value.

BRIEF DESCRIPTION OF THE DRAWINGS

These and other objects and features of the present invention will become readily understood from the following detailed description thereof taken in conjunction the preferred embodiments of the present invention with in the drawings. FIGS. 1 to 16 pertains to a first preferred embodiment of the present invention and FIGS. 17 to 29 pertain to a second preferred embodiment of the present invention.

FIG. 1 is a schematic fluid circuit diagram of a plasma filtration apparatus according to a first preferred embodiment of the present invention showing the principle thereof;

FIG. 2 is a fluid circuit diagram of the plasma filtration apparatus showing a condition in which whole blood is being processed;

FIGS. 3 and 4 are schematic side and front elevational views of the plasma filtration apparatus;

FIG. 5 is a fluid circuit diagram of the plasma filtration apparatus according to the first preferred embodiment of the present invention;

FIGS. 6 to 13 are schematic fluid circuit diagrams showing the sequence of operation of the plasma filtration apparatus according to the first preferred embodiment of the present invention;

FIGS. 14 to 16 are flow charts showing the method of controlling the plasma filtration apparatus according to the first preferred embodiment of the present invention;

DETAILED DESCRIPTION OF THE PREFERRED EMBODIMENTS

Throughout the several views of the accompanying drawings, like parts are designated by like references for the purpose of facilitating the ready understanding of the present invention.

Figure 1:
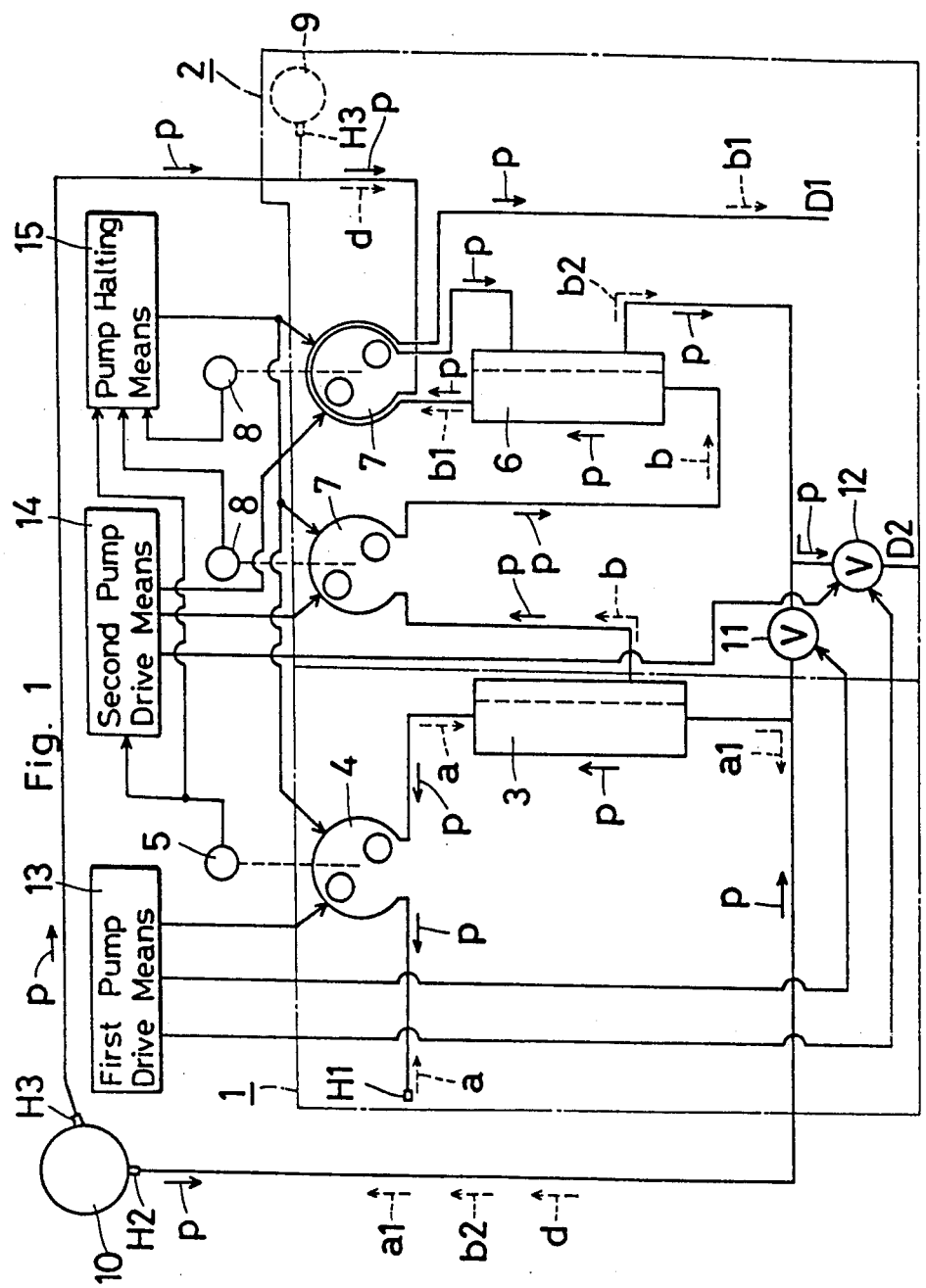

Referring first to FIG. 1 showing the principle of the plasma filtration apparatus according to a first preferred embodiment of the present invention, a blood circulating circuit 1 includes a plasma filter 3 for separating whole blood a, extracted from, for example, a patient through a blood inlet H1 into a blood corpuscle component a1 and a blood plasma component b, a first pump 4, and a first detector 5 for detecting the flow of whole blood in the blood circulating circuit 1, and is so designed as to return the blood corpuscle component a1 to the patient through a blood outlet H2.

A plasma circulating circuit 2 includes a plasma component filter 6 for separating the blood plasma component b, which has been filtered by the plasma filter 3, into a high molecular component b1 and a low molecular component b2, a second pump 7, and a second detector 8 for detecting the flow of the plasma component in the plasma circulating circuit 2, and is so designed as to drain the high molecular component b1 to the outside through a drain opening D1 and also to return the low molecular component b2 to the patient through a downstream portion of the blood circulating circuit 1 downstream of the plasma filter 3 with respect to the direction of flow of the fluid towards the blood outlet H2. It is to be noted that the plasma component filter 6 is adapted to be fluid-connected with a source 9 of physiologically compatible solution, such as albumin or HES, so that a quantity of physiologically compatible solution d supplied to the plasma component filter 6 can mix with the low molecular component b2 prior to the latter being returned to the patient.

The plasma filter 3 referred to above has a corpuscle outlet and is supported in an upright position with the corpuscle outlet positioned downwards, whereas the plasma component filter 6 has a plasma inlet and is supported in an upright position with the plasma inlet positioned downwards. Both of the filters 3 and 6 are normally supported in an upright position, i.e., oriented vertically, but may be supported in an inclined fashion with their corpuscle and plasma inlets so positioned as to orient downwards.

Reference numeral 10 represents a source of priming fluid, such as normal saline solution, to which the blood outlet H2 and a solution intake H3 are adapted to be connected to link the supply of the priming solution p to the blood circulating circuit 1 and the plasma circulating circuit 2. Between a downstream portion of the plasma circulating circuit 2 and a downstream portion of the blood circulating circuit 1 downstream of the plasma filter 3, there is disposed a first valve 11 for selectively establishing and interrupting a fluid circuit therebetween, and a second valve 12 is disposed on the downstream portion of the plasma circulating circuit 2 for selectively establishing and interrupting a fluid circuit between it and the outside of the system.

The plasma filtration apparatus also comprises a first and second pump drive means 13 and 14, and a pump halting means 15. In response to the application of an external start signal, the first and second valves 11 and 12 are closed and the first pump 4 is reversed, i.e., driven so as to rotate in a direction counterclockwise as viewed in FIG. 1, so that the priming fluid p can be supplied into the blood circulating circuit 1 so as to flow across the plasma filter 3 in a direction from the lower end to the upper end thereof. The second pump drive means 14 when receiving a detection signal from the first detector 5 indicating that the flow of the priming fluid p through the blood circulating circuit 1 has attained a predetermined value, opens the second valve 12 and drives the second pump 7 so that the priming fluid p can flow across the plasma component filter 6 in a direction from the lower end to the upper end thereof. The pump halting means 15 is operable, when detection signals from the first and second detectors 5 and 8 are received indicating that the flow of the primary fluid p in the blood circulating circuit 1 and that in the plasma circulating circuit 2 have attained a second predetermined value, respectively, to bring the first and second pumps 4 and 7 to a halt, thereby completing the priming operation.

According to the above described construction, as the priming fluid p flows through the plasma filter 3 from the lower end to the upper end thereof, air contained in the plasma filter 3 can be smoothly expelled outside the system through the blood inlet H1, and as the priming fluid p subsequently flows through the plasma component filter 6 from the lower end to the upper end thereof, air also contained in the plasma component filter 6 can be smoothly expelled outside the system. During a period subsequent to the supply of the priming fluid p into the blood circulating circuit 1 and before the attainment of the flow of the priming fluid p in the blood circulating circuit 1 to the first predetermined value, the first and second valves 11 and 12 are closed with no priming fluid p consequently flowing in the plasma component filter 6 and, therefore, air contained in the blood circulating circuit 1 can be smoothly expelled to the outside of the system during that period with no possibility of the air entering the plasma circulating circuit 2.

Moreover, the priming fluid p which has been contaminated as a result of the flow thereof through the plasma circulating circuit 2 can be discharged to the outside of the system through the second valve 12 and, therefore, there is little possibility that contaminants contained in the priming fluid p will enter the blood circulating circuit 1.

Since the priming fluid p flows through the blood circulating circuit 1 and the plasma circulating circuit 2 until the flow in the blood circulating circuit 1 and that in the plasma circulating circuit 2 attain the second predetermined value, both can be effectively and satisfactorily cleansed.

Hereinafter, a first preferred embodiment of the present invention will be described, it being noted, however, that before the description of the priming system according to the present invention, the structure of the blood processing apparatus will first be described.

Figure 2:
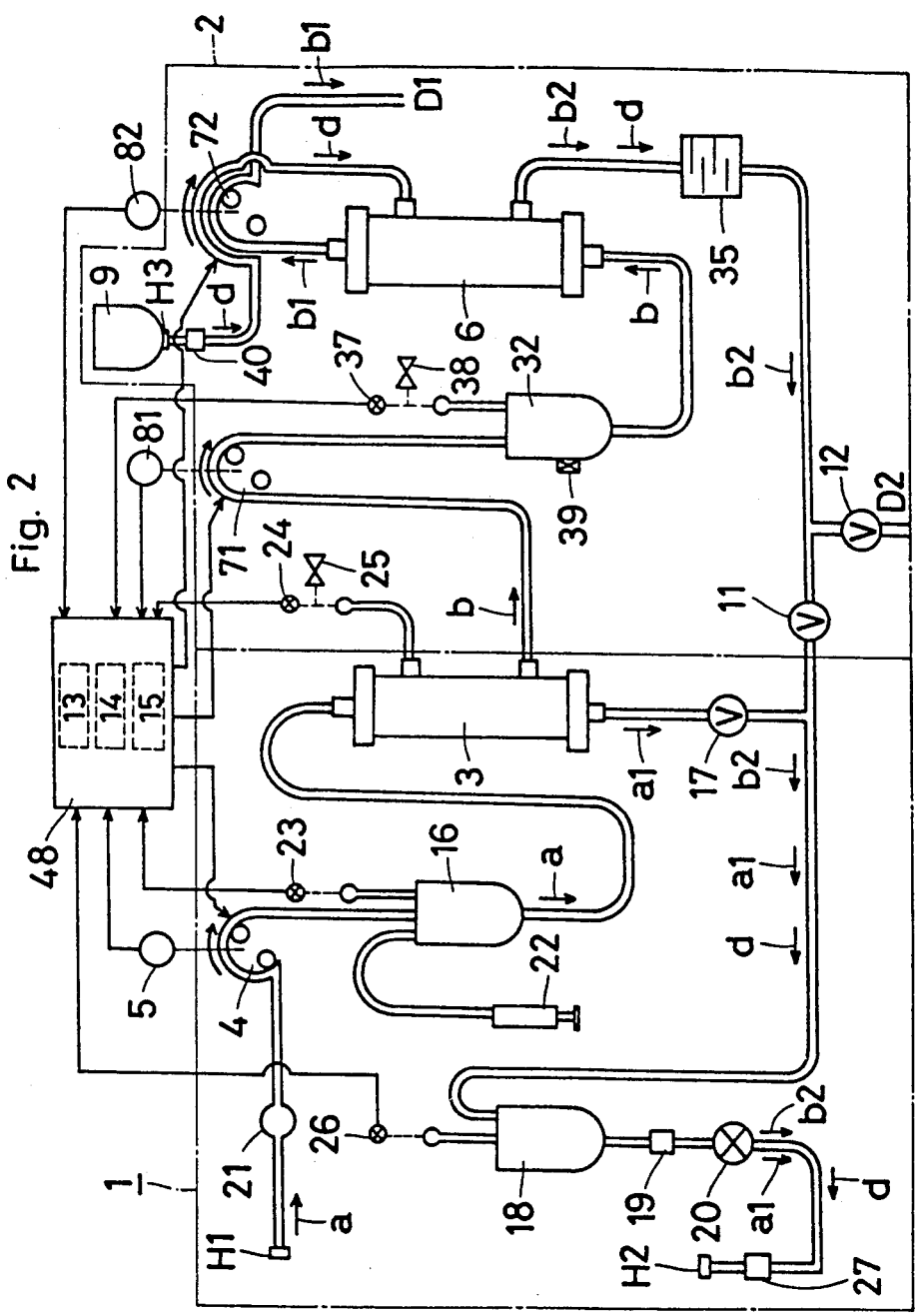

Referring to FIG. 2, whole blood a extracted into the blood circulating circuit 1 through the blood inlet H1 which may be constituted by a coupled connectable with a shunt, a cannule, a syringe needle or a blood reservoir is, after the pressure thereof has been increased by the first pump 4, that is, a blood pump, supplied into an arterial pressure chamber 16 and then towards an upper end of the plasma filter 3 which is supported in upright position so as to extend vertically. The whole blood a supplied into the plasma filter 3 from the upper end thereof is separated into the corpuscle component a1 and the plasma component b within the plasma filter 3. The plasma filter 3 may be of any known construction having a semi-permeable, plasma separating membrane, for example, a plate-like, tubular or hollow fiber separating membrane made of a copolymer of polyvinyl alcohol (PVA), preferably the separating membrane comprised of a bundle of hollow fibers is usually employed in the plasma filter 3.

The corpuscle component a1 separated from the whole blood in the plasma filter 3 is supplied into a venous pressure chamber 18 through a first blood valve 17 and is subsequently supplied through a bubble detector 19 and then through a second blood valve 20 to the blood outlet H2 which may be constituted by a coupler connectable with a shunt, a cannule or an instillation unit.

A pillow sensor 21 comprised of an expandable bag is disposed upstream of the blood pump 4 with respect to the direction of flow of whole blood towards the plasma filter 3. This pillow sensor 21 is operable in response to a change in blood pressure in the blood flow path in the event that a difficulty arises in blood extraction in such a way that, when it detects the presence of a negative pressure in the blood flow path, the blood pump 4 can be brought to a halt, but when it detects that the negative pressure has been removed, the blood pump 4 once brought to a halt can be restarted. The arterial pressure chamber 16 is connected with a heparine injector 22 for injecting a small quantity of heparing thereinto to mix with the whole blood for avoiding any possible coagulation of the blood being processed, and an arterial pressure sensor 23. The plasma filter 3 is connected with a filtration pressure sensor 24 and an air introducing valve 25. On the other hand, the venous pressure chamber 18 is connected with a venous pressure sensor 26. A blood flow path between the venous pressure chamber 18 and the blood outlet H2 has a bubble detector 27 disposed therein and located in the vicinity of the blood outlet H2.

The plasma component b separated from the whole blood in the plasma filter 3 is, after the pressure thereof has been increased by a plasma pump 71 disposed in the plasma circulating circuit 2, supplied into a secondary membrane pressure chamber 32 and then into the plasma component filter 6. As is the case with the plasma filter 3, the plasma component filter 6 is supported in an upright position so as to extend vertically, and therefore, the plasma supplied from the secondary membrane pressure chamber 32 is supplied thereinto from an upper end thereof and is then separated in the plasma component filter 6 into a high molecular component b1 and a low molecular component b2. The plasma component filter 6 may be of any known construction having a semi-permeable plasma processing membrane, for example, a plate-like, tubular or hollow filter separating membrane made of a copolymer of ethylenevinyl alcohol (EVA), preferably the separating membrane comprised of a bundle of hollow fibers is usually employed in the plasma component filter 6.

The high molecular component b1 separated from the plasma in the plasma component filter 6 is pumped to the outside of the system by a drain pump 72 after having outflowed from an upper end of the plasma component filter 6 and then through a drain opening D1. On the other hand, the low molecular component b2 flows towards a downstream portion of the blood circulating circuit 1 downstream of the plasma filter 3 and then towards the blood outlet H2 after having flowed through a heating unit 35 comprised of an electric heater. It is to be noted that the plasma pump 71 and the drain pump 72 together constitute the second pump 7 referred to in connection with the principle of the present invention.

The secondary membrane pressure chamber 32 is connected with a secondary membrane pressure sensor 37, an air discharge valve 38 and a liquid level sensor 39, and the plasma component filter 6 has the solution intake H3, which may be comprised of a coupler connectable with an instillation unit, connected therewith through the drain pump 72 and a bubble detector 40. The solution intake H3 is in turn connected to a source of physiologically compatible solution 9 from which a physiologically compatible solution d such as albumin or HES can be supplied by the drain pump 72 into the plasma component filter 6 to mix with the low molecular component b2.

A fluid path between a downstream portion of the plasma circulating circuit 2 downstream of the plasma component filter 6 and a downstream portion of the blood circulating circuit 1 downstream of the plasma filter 3 is provided with the first valve 11 for selectively establishing and interrupting the circuit, and a downstream portion of the plasma circulating circuit 2 upstream of the first valve 11 has a branch passage ramified therefrom and provided with the second valve 12 for selectively establishing and interrupting a fluid circuit between the downstream side of the plasma component filter 6 and the outside of the system.

The blood pump 4, the plasma pump 71 and the drain pump 72 are operatively coupled with a blood flow detector 5, a plasma flow detector 81 and a drain flow detector 82, respectively. The blood flow detector 5 is operable to detect the flow of whole blood through the blood circulating circuit 1 in terms of the number of revolutions of the blood pump 4. The plasma flow detector 81 is operable to detect the flow of plasma through the plasma circulating circuit 2 in terms of the number of revolutions of the plasma pump 71, and the drain flow detector 82 is operable to detect the flow of the fluid to be drained in terms of the number of revolutions of the drain pump 72.

Flow signals from the detectors 5, 81 and 82 and pressure signals from the pressure sensors 23, 24, 26 and 37 are all fed to a control device 48 comprising a microcomputer which monitors these signals to control, during the clinical use of the apparatus, the respective number of revolutions of the pumps 4, 71 and 72 for bringing the flow rate in the blood circulating circuit 1, the flow rate in the plasma circulating circuit 2, the membrane pressure in the plasma filter 3 and the membrane pressure in the plasma component filter 6 to their respective proper values. While the drain pump 72 is concurrently used to drain the high molecular component b1 to the outside and to supply the physiologically compatible solution d into the plasma circulating circuit 2, it may be contemplated to use two separate pumps for draining the high molecular component b1 and for supplying the physiologically compatible solution d, respectively. However, the concurrent use of the drain pump 72 for these two purposes such as in the illustrated embodiment of the present invention is advantageous in that, with no need to control the drain pump 72 in two different ways for the respective functions, the amount of the high molecular component b1 drained and that of the physiologically compatible solution d supplied can be equalized with each other at all times.

Both the blood circulating circuit 1 and the plasma circulating circuit 2 are installed at a front panel 50a of a caster-equipped console 50 as shown in FIGS. 3 and 4. As best shown in FIG. 4, the front panel 50a of the caster-equipped console 50 has mounted thereon both of the blood circulating circuit 1 and the plasma circulating circuit 2, each including a corresponding number of tubings made of, for example, polyvinyl chloride, with the plasma filter 3, the plasma component filter 6 and the other component parts being interposed therein. At top of the caster-equipped console 50, there is disposed a contaol panel having various control knobs for issuing commands necessary to control the blood pump 4, the plasma pump 71 and the drain pump 72, which control panel also includes a display unit 51 for displaying data being monitored and a description representative of the sequence of manipulation to be carried out.

The priming operation to be carried out using the blood processing apparatus of the construction described hereinabove will now be described.

Figure 5:
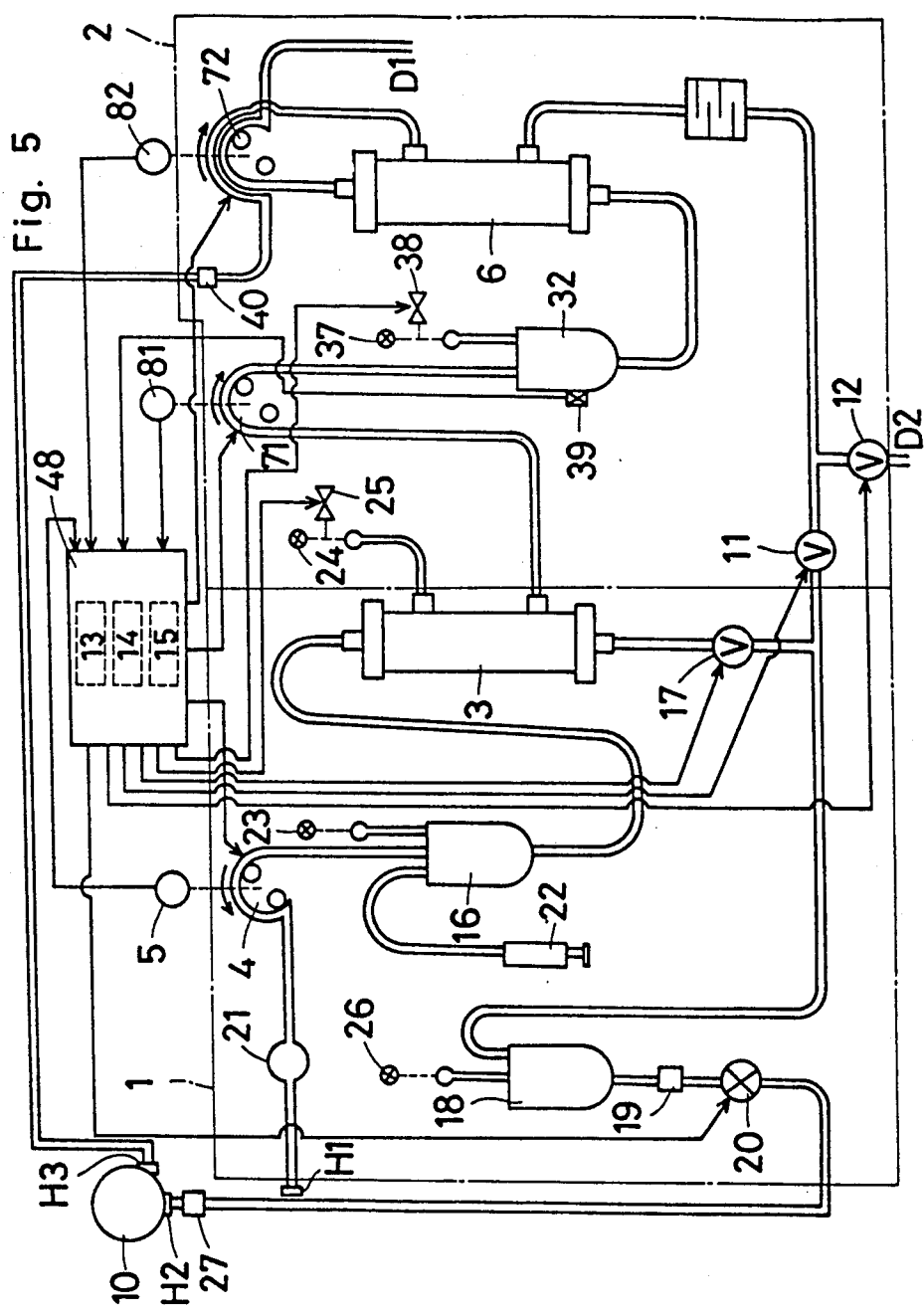

Referring to FIG. 5, the blood outlet H2 is fluid-connected through the bubble detector 27 with a source 10 of priming solution, i.e., normal saline solution, and the solution intake H3 upstream of the bubble detector 40 is fluid-connected with the priming solution source 10 in place of the physiologically compatible solution source 9 (FIG. 2). The control device 48 has built therein a first pump drive means 13 for driving the blood pump 4, a second pump drive means 14 for driving both the plasma pump 71 and the drain pump 72, and a pump halting means 15.

Figure 6:
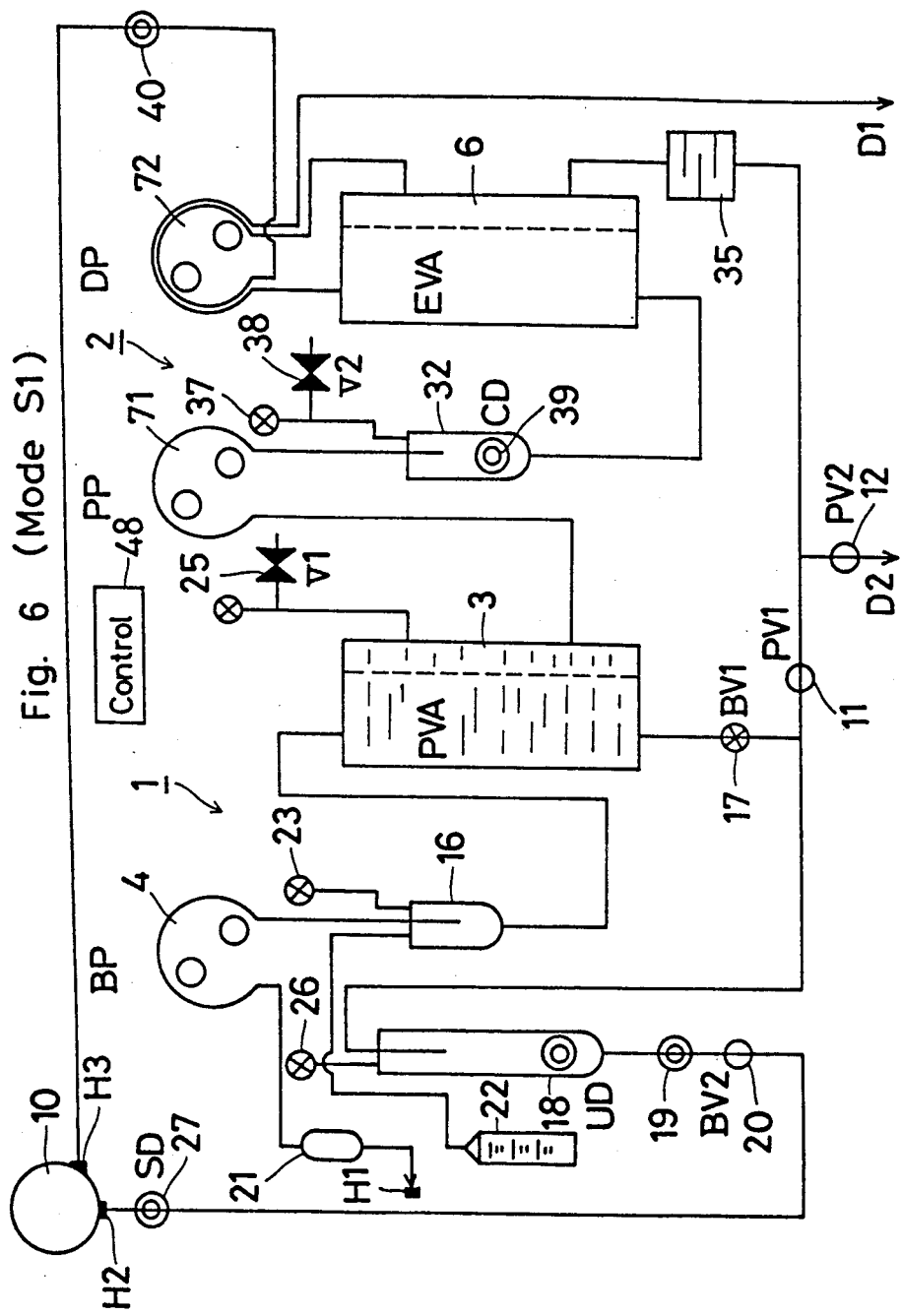

On the other hand, since the plasma filter 3 is normally filled with normal saline solution or distilled water, the first blood valve 17 is, at the outset of the priming operation, closed to enable the plasma filter 3 to be set in position with no possibility of the solution or water leaking out from the plasma filter 3, thereby avoiding any possible entry of air into the plasma filter 3. This condition of the system is shown in FIG. 6 and is hereinafter referred to as Mode S1 ready for the actual use of the apparatus for the priming operation.

Figure 7:
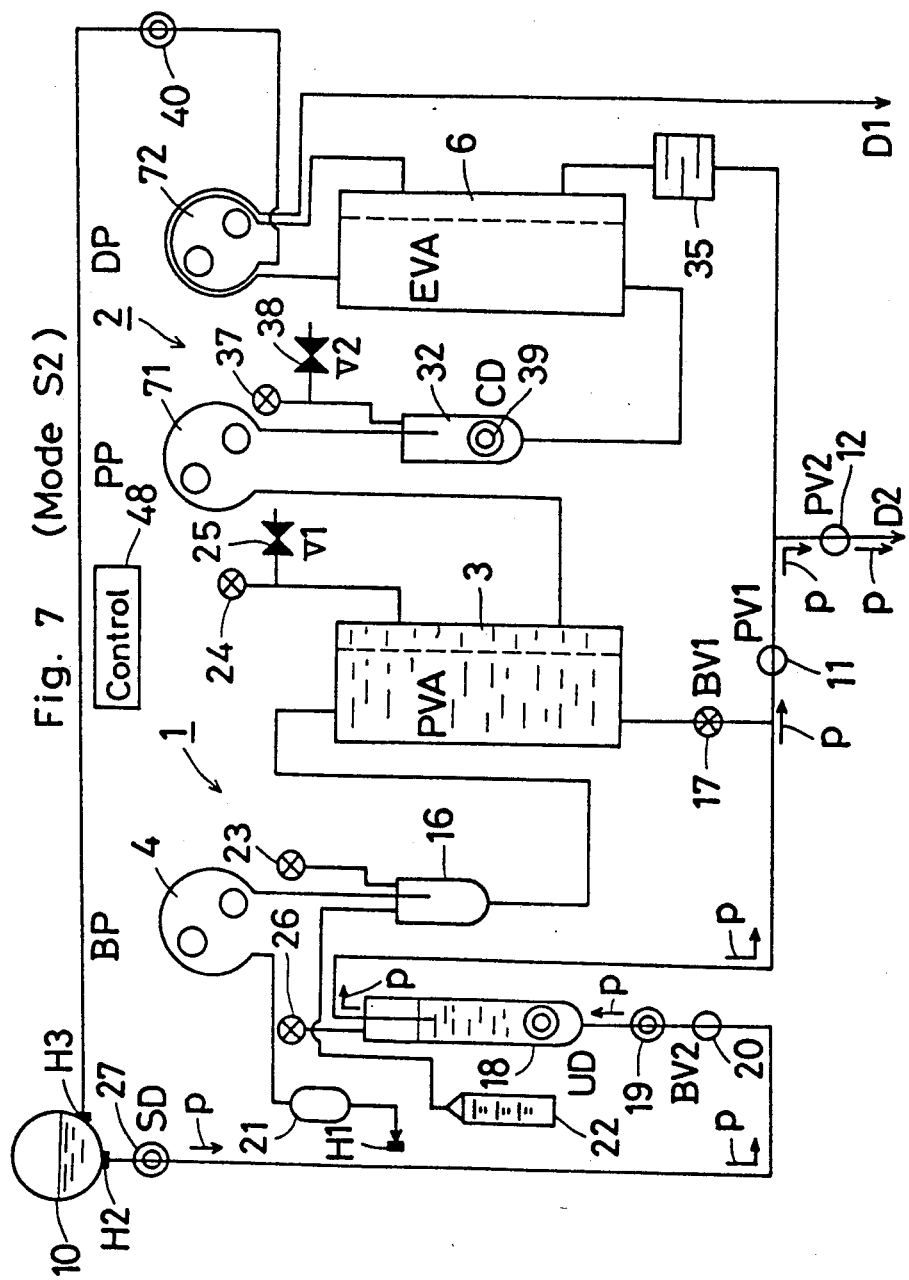

The sequence of the priming operation carried out using the apparatus is shown in FIGS. 7 to 13, reference to which will now be made. FIG. 7 illustrates another condition of the system referred to as Mode S2 in which, while all of the pumps 4, 71 and 72 are held inoperative, the control device 48 is activated in response to an external start signal, applied thereto, to close both the air introducing valve 25 and the air discharge valve 38 and, on the other hand, to open the first valve 11, the second valve 12 and the second blood valve 20. As a result thereof, the priming solution p flows from the priming solution source 10 to the outside of the system through the second blood valve 20, the bubble detector 19, the venous pressure chamber 18, the first valve 11, and the second valve 12 and finally through the drain opening D2 in the order specified above with the consequence that air contained in a portion of the blood circulating circuit 1 on the side of the blood outlet H2 can be expelled to the outside of the system.

Figure 8:
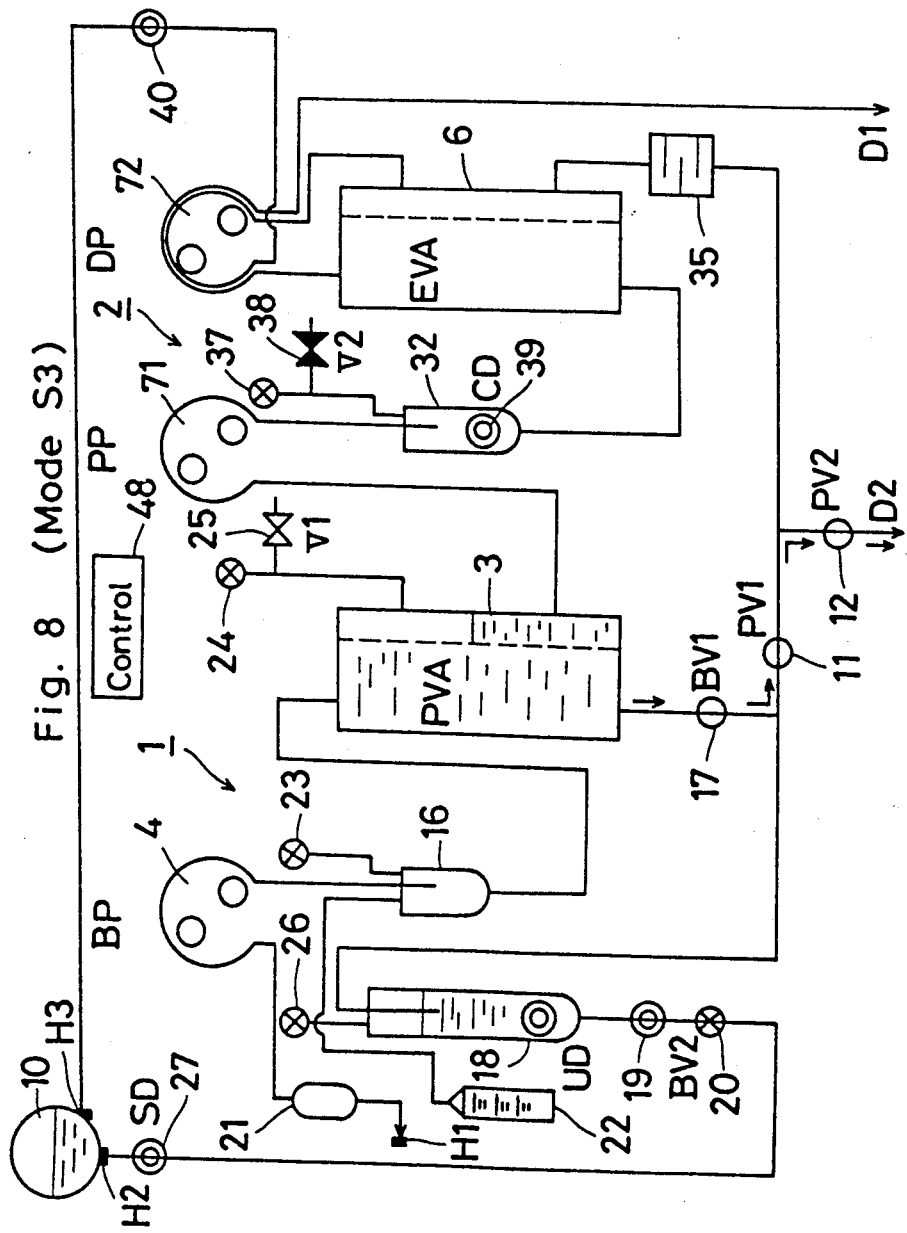

During the subsequent condition shown in FIG. 8 and referred to as Mode S3, the second blood vave 20 and both the air introducing valve 25 and the first blood valve 17 are closed and opened, respectively, in response to associated command signals generated from the control device 48. Although it seems that the opening of the air introducing valve 25 permits the entry of air therethrough towards the plasma filter 3, no air will in actually enter the hollow interior of the plasma filter 3. Therefore, during Mode S3 shown in FIG. 8, only the solution with a plasma chamber of the plasma filter 3 is allowed to permeate into the hollow fibers and is subsequently discharged to the outside through the first blood valve 17, then, the first valve 11 and, finally, the second valve 12.

Figure 9:
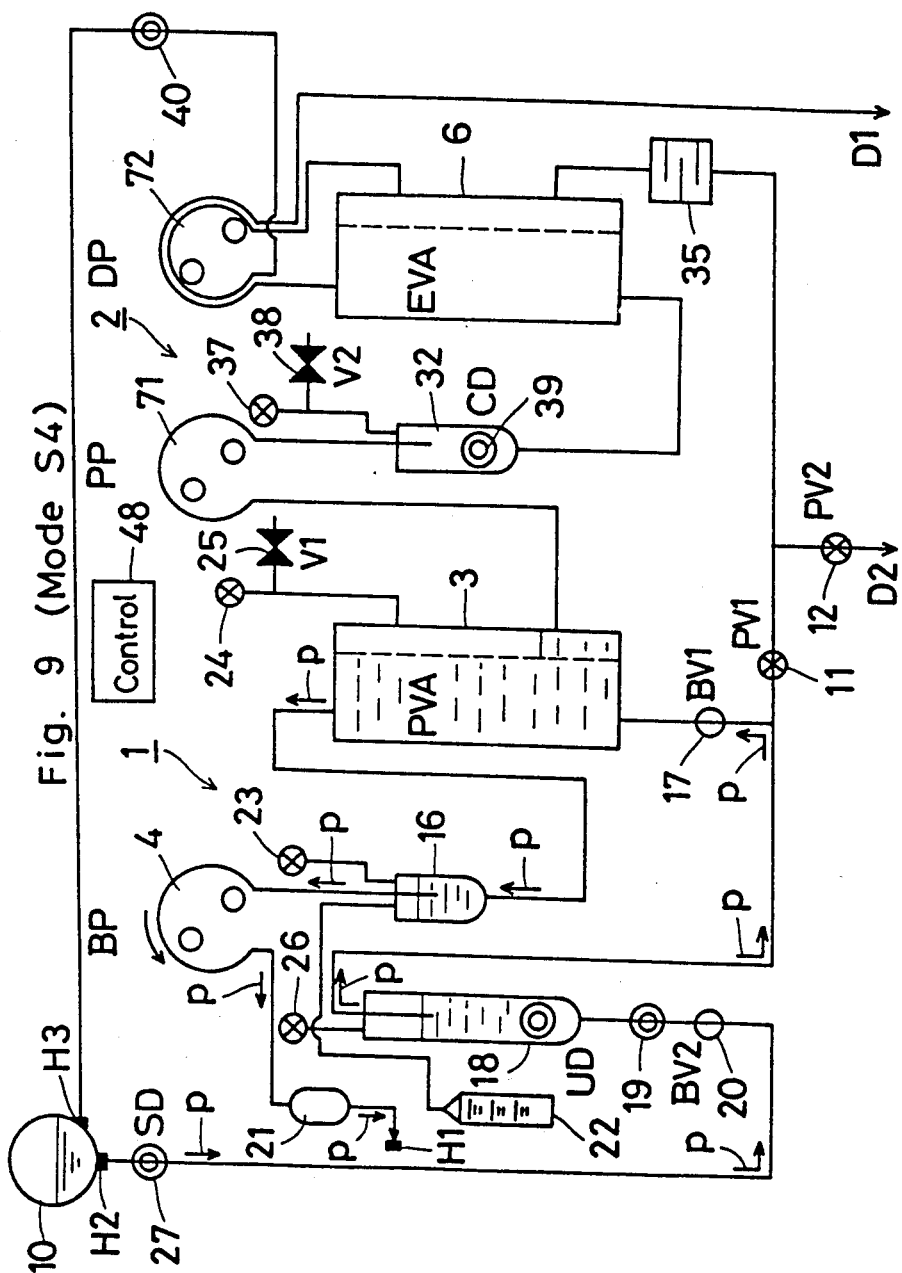

During Mode S4 shown in FIG. 9, the control device 48 causes the second blood valve 20 and the first blood valve 17 to open and the air introducing valve 25 and the first and second valves 11 and 12 to close and also causes the blood pump 4 to reverse its direction of rotation so that the priming solution p can flow through the entire blood circulating circuit 1 for cleansing the fluid circuit components and also for expelling air contained therein. Since at this time the priming solution p flows across the plasma filter 3 in a direction from the lower end to the upper end thereof, air contained in the plasma filter 3 can be smoothly expelled out of the plasma filter 3 and then discharged to the outside through the arterial pressure chamber 16, the blood pump 4, the pillow sensor 21 and finally the blood inlet H1. At the same time, the plasma pump 71 and the drain pump 72 both in the plasma circulating circuit 2 are held inoperative with no priming solution p consequently flowing in the plasma circulating circuit 2 and, therefore, there is no possibility that air present in the downstream portion of the blood circulating circuit 1 downstream of the plasma filter 3 will enter the plasma circulating circuit 2.

Figure 10:
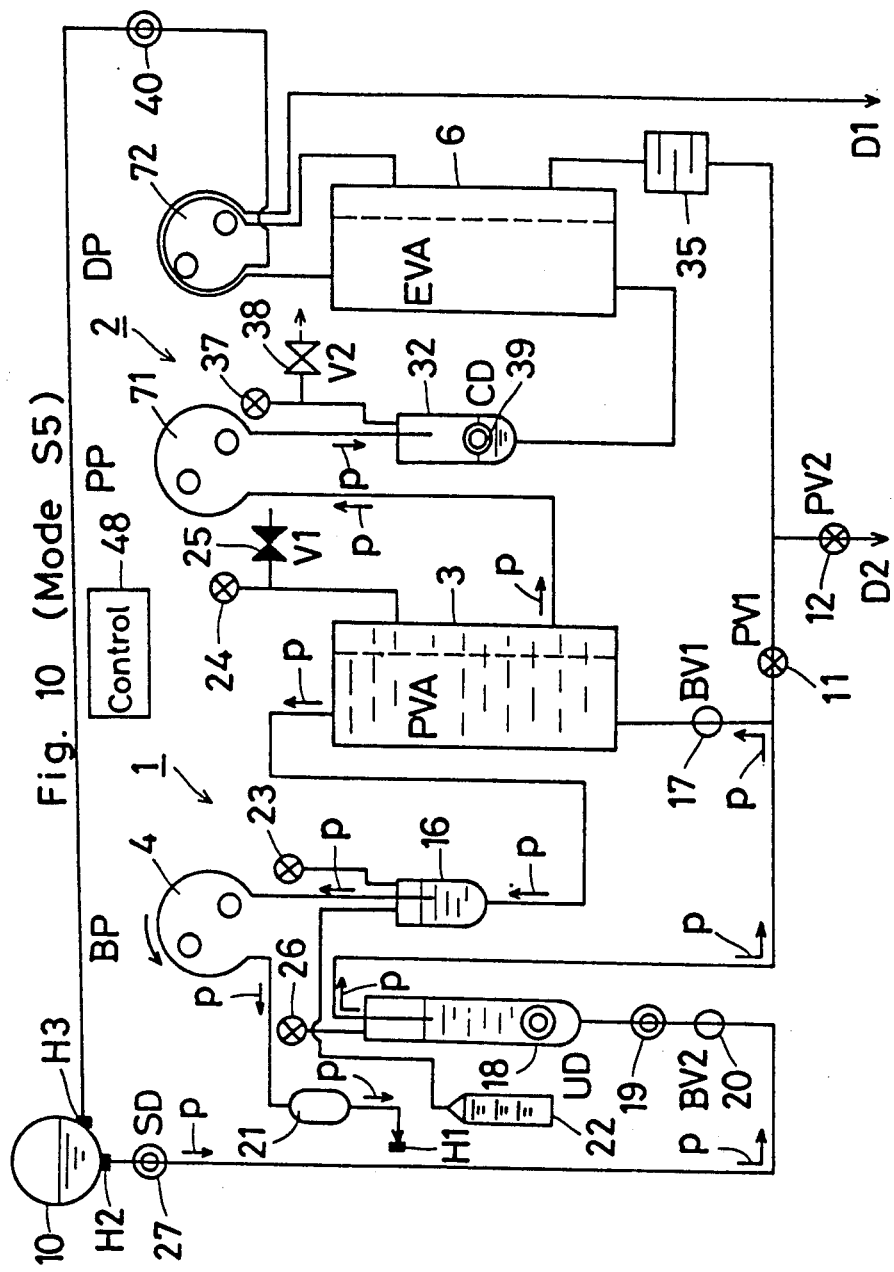

When the flow output generated from the blood flow detector 5 (FIG. 5) applied to the control device 48 indicates that the flow rate in the blood circulating circuit 1 has attained a first predetermined value, this means that air in the blood circulating circuit 1 has been completely expelled to the outside of the system and, therefor, Mode S5 shown in FIG. 10 takes place. As shown in FIG. 10, during Mode S5, the control device 48 generates commands necessary to open the air discharge valve 38 in the plasma circulating circuit 2 and to drive the plasma pump 71 in a first direction required to permit the priming solution p to be supplied from the plasma filter 3 to the secondary membrane pressure chamber 32.

Figure 11:
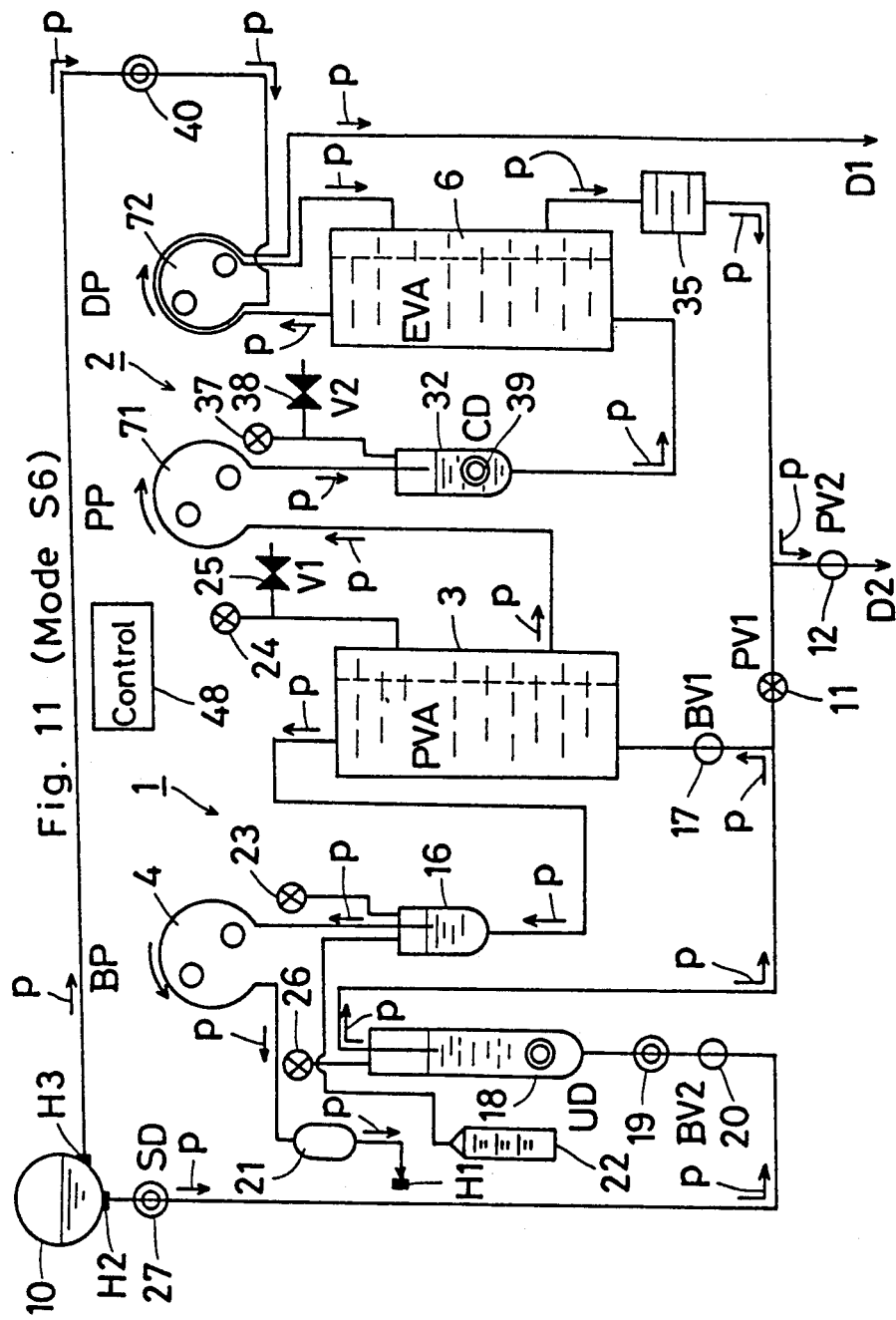

During the period in which the liquid level sensor 39 in the secondary membrane pressure chamber 32 does not detect the level of the priming solution p within the chamber 32, the control device 48 opens the air discharge valve 38 and drives the drain pump 72 in a first direction at a velocity necessary to attain a predetermined discharge rate lower than, for example, half the discharge rate of, the plasma pump 71 to supply a portion of the priming solution p to the plasma component filter 6 while the remaining portion of the priming solution p remains filling the secondary membrane pressure chamber 32. At this time, the priming solution p is also supplied from drain pump 72 to the plasma component filter 6 through the solution inlet H3 by way of the bubble detector 40. When the liquid level sensor 39 detects the level of the priming solution p in chamber 32, that is, when the secondary membrane pressure chamber 32 has been sufficiently filled with the priming solution p, the next subsequent Mode S6 shown in FIG. 11 is started wherein the control device 48 causes the air discharge valve 38 and the second valve 12 to close and open, respectively, and on the other hand to drive drain pump 72 in the first direction so as to attain the same discharge rate as that of plasma pump 71, thereby allowing the priming solution p to sufficiently pass through the plasma component filter 6.

Figure 12:
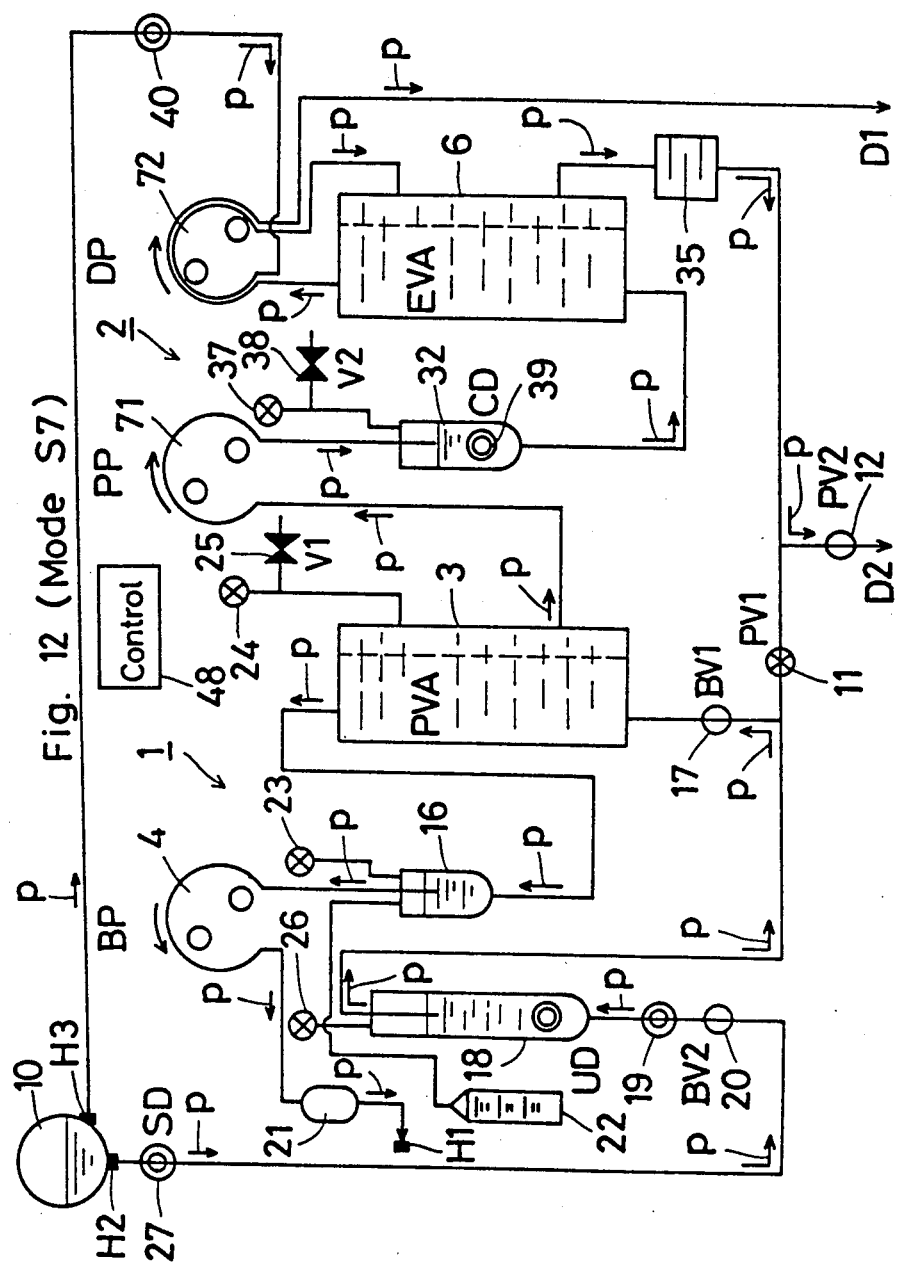
Figure 13:
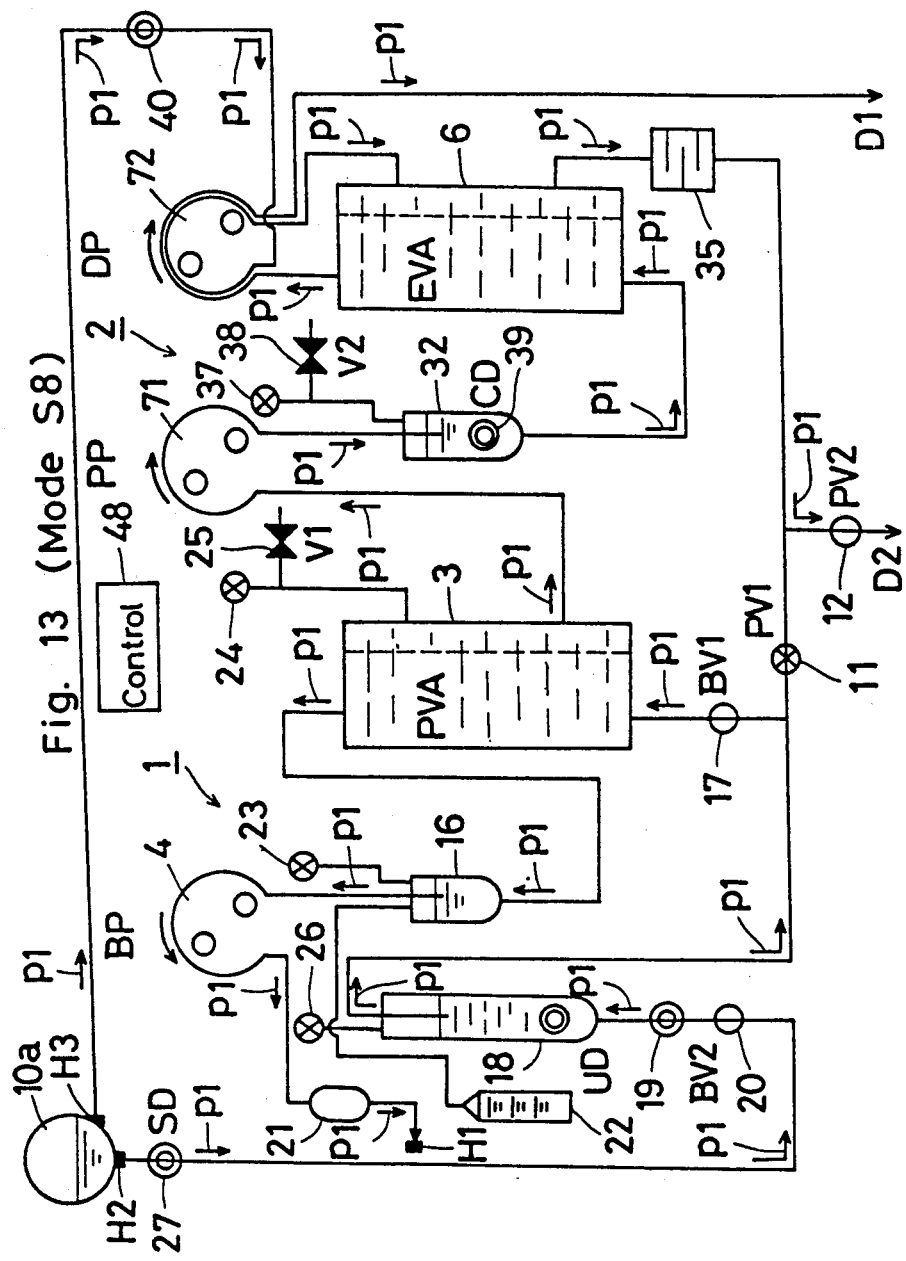

Thereafter, as shown in FIG. 12 showing Mode S7, when the level of the priming solution within the secondary membrane pressure chamber 32 lowers below a predetermined level, there is a possibility that air may enter the chamber 32 to mix with the priming solution p. At this time, the liquid level sensor 39 generates an output signal indicative of the lowering of the liquid level past the predetermined level, which output signal is applied to the control device 48 to cause the latter to close and open the second valve 12 and the air discharge valve 38, respectively, so that the secondary membrane pressure chamber 32 can be filled with the primary solution p while the air contained in the secondary membrane pressure chamber 32 is expelled to the outside through the air discharge valve 38. When the liquid level sensor 39 subsequently again detects the level of the priming solution p with the secondary membrane pressure chamber 32, that is, when the priming solution p is filled within the secondary membrane pressure chamber 32 again to the predetermined level, the control device 48 causes the second valve 12 and the air discharge valve 38 to open and close respectively. This control is referred to as "CD Control" in a block of the process step P16 shown in the flow chart as will be described later with particular reference to FIG. 16.

When intelligence derived from the respective output signals from the blood flow detector 5, the plasma flow detector 81 and the drain flow detector 82 indicates that both the flow rate in the blood circulating circuit 1 and the flow rate in the plasma circulating circuit 2 has attained a predetermine value, the control device 48 causes the display unit 51 (FIG. 4) to display an indication that the priming with the priming solution mixed with heparin should be carried out, while triggering a warning device, for example, a chime, to call the attention of an operator of the apparatus. The operator then acts, in response to the visual indication displayed in the display unit 51 and/or the audio indication issued by the warning device, to disconnect the priming solution source 10 from the system and to connect a source 10a of priming solution p1 mixed with heparin, this condition being shown in FIG. 13 and referred to as Mode S8. Thereafter, the normal operation under Mode S7 shown in FIG. 12 is continued. It is to be noted that for the purpose of the subsequent description the priming solution p1 mixed with the heparin which is supplied from the priming solution source 10a is hereinafter referred to as "mixed priming solution".

When the output signals from the blood flow detector 5, the plasma flow detector 81 and the drain flow detector 82 applied thereto indicate that the cumulative flow of the primary solution p and the mixed priming solution p1 both having flowed through the blood circulating circuit 1 and the plasma circulating circuit 2 have attained a second predetermined value, the control device 48 determines that the cleansing of and the removal of air from both the blood circulating circuit 1 and the plasma circulating circuit 2 have finished, and brings all of the pumps 3, 71 and 72 to a halt, thereby completing the priming cycle.

Figure 15:
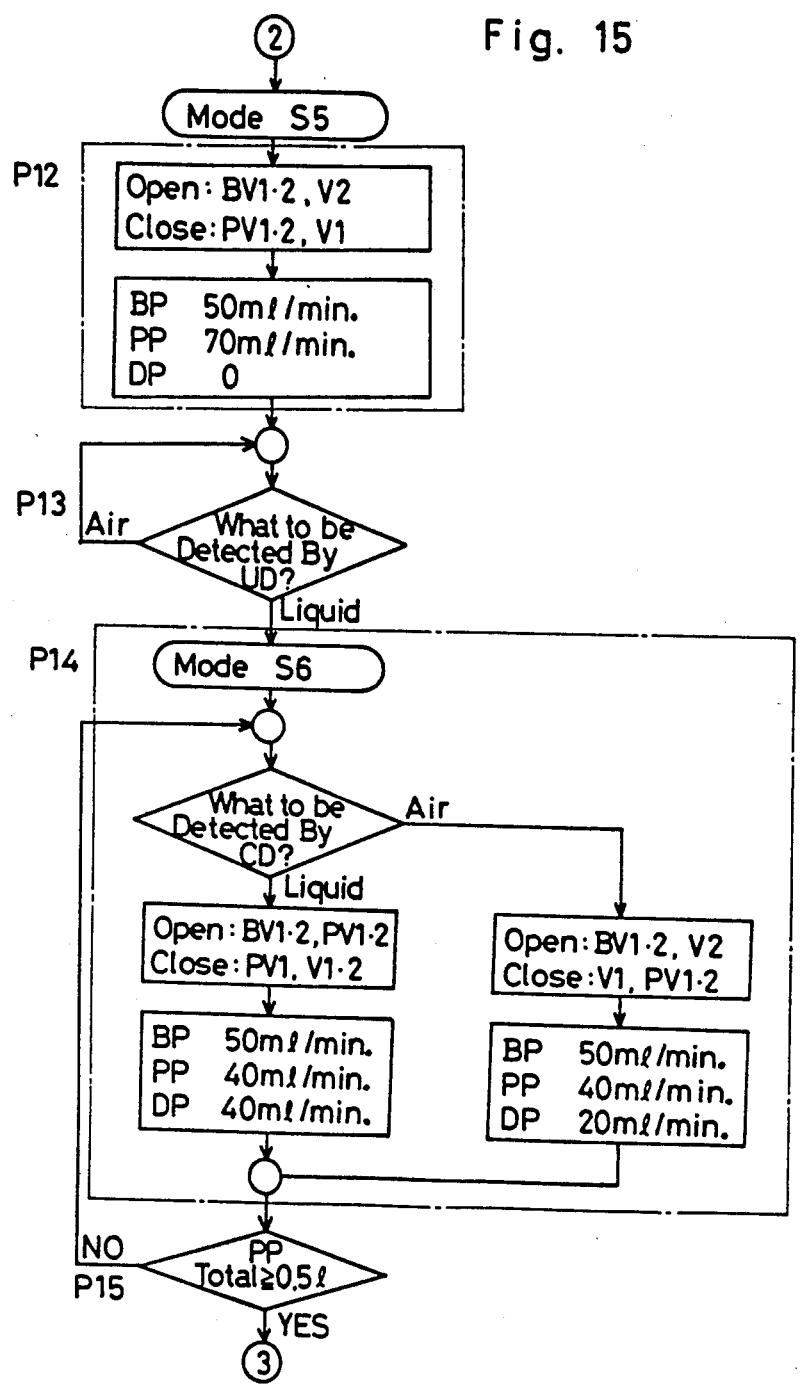

Hereinafter, the priming cycle executed by the control device 48 will be described with reference to the flow charts shown in FIGS. 14 to 16. Before the description proceeds, the following abbreviations used in the flowcharts are used to denote the following respective component parts of the apparatus.

PV1 stands for the first valve 11; PV2 for the second valve 12; BV1 for the first blood valve 17; BV2 for the second blood valve 20; V1 for the air introducing valve 25; V2 for the air discharge valve 38; UD for the venous pressure chamber 18; SD for the bubble detector 27; CD for the liquid level sensor 39 in the secondary membrane pressure chamber 32; BP for the blood pump 4; PP for the plasma pump 71; and DP for the drain pump 72.

Referring first to FIG. 14 and subsequent to the start at step P1, Mode S1 (FIG. 6) takes place at step P2 in readiness for the actual priming cycle. After the initialization at step P3, a decision is made at step P4 to determine if a start button (not shown) has been depressed. If the start button has been depressed, the program flow proceeds to step P5 at which Mode S2 (FIG. 7) takes place. As hereinbefore described, during Mode S2, BV2, PV1 and PV2 are all opened and BV1, V1 and V2 are all closed so that the air contained in the downstream portion of the blood circulating circuit 1 can be expelled to the outside.

Subsequently, step P6 is executed at which a decision is made to determine if UD has detected the level of the priming solution within the secondary membrane pressure chamber 32. When and after UD has detected the level of the priming solution within the secondary membrane pressure chamber 32, the control device 48 waits for, for example, 30 seconds at step P7, which time is required to complete the total removal of air from the blood circulating circuit 1.

The program flow then proceeds to step P8 at which Mode S3 (FIG. 8) takes place. During this Mode S3, BV1, PV1, PV2 and V1 are all opened and BV2 and V2 are closed as hereinbefore described, so that the distilled water remaining within the plasma component filter 3 is removed. The removal of the distilled water continues for, for example, one minutes at step P9.

Thereafter, step P10 is executed at which Mode S4 (FIG. 9) takes place. As hereinbefore described, during Mode S4, BV1 and BV2 are opened, PV1, PV2, V1 and V2 are closed and BP is reversed, i.e., driven in a second direction opposite to the first direction, so as to attain the discharge rate of, for example, 120 ml per minute to effect the supply of the priming solution p throughout the blood circulating circuit 1. At step P11, a decision is made to determine if the cumulative discharge amount of BP, that is, the cumulative flow rate in the blood circulating circuit 1, has exceeded a first predetermined value, for example, 0.3 ml. In the event that the result of the decision at step P11 indicates the excess of the cumulative flow rate over the first predetermined value, this means that the air in the blood circulating circuit 1 has been completely removed, and therefore, the program flow proceeds to step P12 shown in FIG. 15, during which step P12 Mode S5 (FIG. 10) take place. As hereinbefore described, during this Mode S5, BV1, BV2 and V2 are opened, PV1, PV2 and V1 are closed, BP is driven in a second direction reverse to the first direction so as to discharge at a rate of, for example, 50 ml per minute and PP is driven in the first direction so as to discharge at a rate of, for example, 70 ml per minute, thereby to supply the priming solution p to the secondary membrane pressure chamber 32.

When CD detects the priming solution p at step P13, the program flow proceeds to step P14 at which Mode S6 (FIG. 11) takes place. During Mode S6, and in the event that CD detects the presence of air because of the level of the priming solution being lower than the predetermined level, BV1, BV2 and V2 are opened while V1, PV1 and PV2 are closed, and at the same time, DP and PP are driven in the first direction so as to attain the ½ discharge rate with respect to each other, so that the priming solution p can be stored in CD. In the event that CD detects the level of the priming solution being higher than the predetermined value, BV1, BV2 and PV2 are opened while PV1, V1 and V2 are closed, and DP and PP are driven in the first direction at the same discharge rate, so that the plasma component filter 6 can be supplied with the priming solution p.

In the event that the cumulative flow from PP has been detected at step P15 as exceeding the predetermined value, for example, 0.5 ml, Mode S7 (FIG. 12) takes place, during which PP and DP are driven in the first direction at a speed required to attain the discharge rates of 70 ml per minute and 10 ml per minute, respectively, to accomplish a normal operation while, at the same time, the CD control as hereinbefore described is in effect to avoid possible suction of air into the plasma component filter 6.

Figure 16:
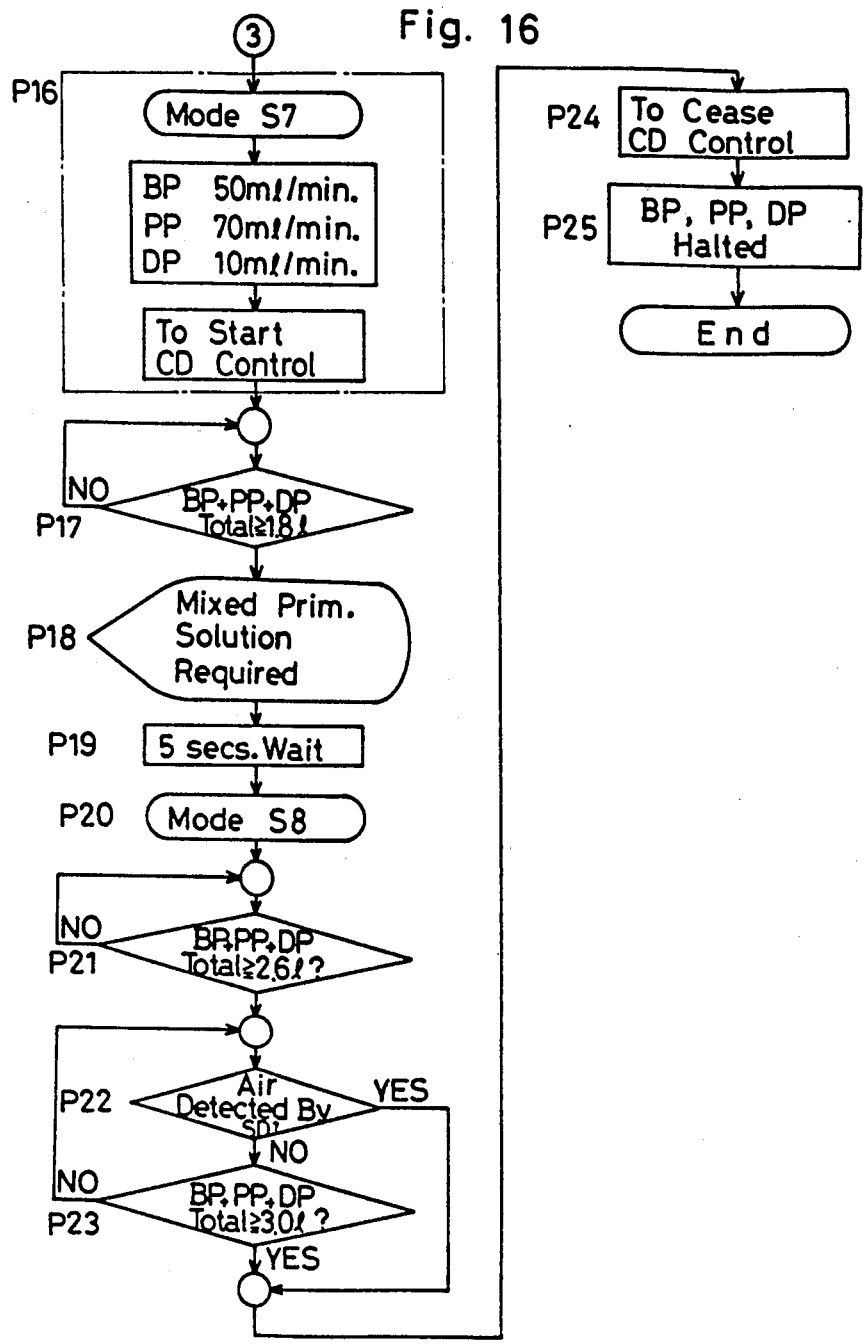

Thereafter, when the cumulative flow from all of BP, PP and DP has been detected at step P17, shown in FIG. 16, as exceeding a predetermined value, for example, 1.8 ml both the removal of air and the cleansing with the use of the priming solution p are deemed as finished, with the program flow consequently proceeding to step P18.

At step P18, the visual indication that the mixed priming solution source should be connected is displayed on the display unit 51 (FIG. 4) and, at the same time, the chime is rung to this effect to call the attention of the operator. When the operator connects the mixed priming solution source, the chime is turned off and a period of about 15 seconds is waited for at subsequent step P19, followed by step P20 during which Mode S8 (FIG. 13) takes place to continue the normal operation as during Mode S7.

Thereafter, and when the cumulative flow from all of BP, PP and DP has been detected at step P21 as attaining a value greater than, for example, 2.6 ml, it can be ascertained that the amount of the priming solution contained in the priming solution source is small and, therefore, SD is brought, at step P22, in position ready to detect the air. If no air is detected by SD, the program flow proceeds to step P23 and, in the event that the cumulative flow from all of BP, PP and DP is detected as exceeding a second predetermined value, for example, 3.0 ml, step P23 is followed by step P24 to interrupt the CD control. On the other hand, if air is detected by CD at step P22, it means that the whole amount of the priming solution has been consumed, and therefore, the program flow proceeds to step P24. Then, at step P25, all of BP, PP and DP are brought to a halt, thereby completing the priming cycle at step P26.

In the foregoing embodiment, the use has been described and shown of two filters, i.e., the plasma filter and the plasma component filter. However, in the practice of the present invention, the plasma component filter may be obviated which will now be described in connection with the second preferred embodiment of the present invention.

The principle of the second embodiment of the present invention will now be described with particular reference to FIG. 17.

Figure 17:
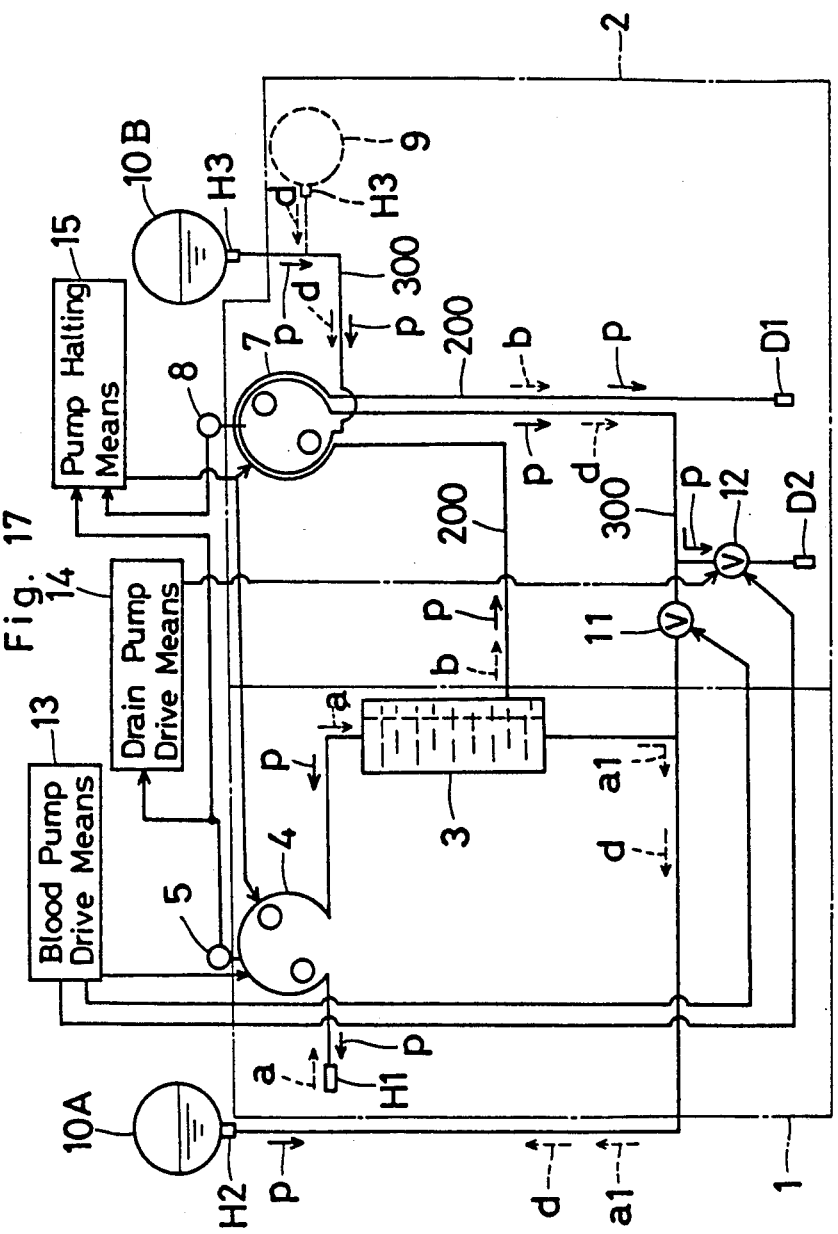
FIG. 17 is a schematic fluid circuit diagram of a plasma filtration apparatus according to the second preferred embodiment of the present invention showing the principle thereof.

As shown in FIG. 17, a blood circulating ciircuit 1 includes the plasma filter 3 for separating whole blood a, extracted from the patient through the blood inlet H1, into the blood corpuscle component a1 and the blood plasma component b, the blood or first pump 4 and the first detector 5 for detecting the flow of whole blood a in the blood circulating circuit 1, and is so designed as to return the blood corpuscle component a1 to the patient through the blood outlet H2.

The plasma filter 3 has a corpuscle outlet and is supported in upright position with the corpuscle outlet positioned downwards. Although the plasma filter 3 is normally suported in upright position, i.e., oriented vertically, it may be supported in an inclined fashion with its corpuscle inlet so positioned as to orient downwards.

A plasma circulating circuit 2 includes a plasma drain passage 200 and a physiologically compatible solution supply passage 300. The plasma drain passage 200 is so designed as to drain the plasma component b to the outside of the system through the drain opening D1 by the action of the drain or second pump 7. The physiologically compatible solution supply passage 300 has the solution inlet H3 connected with a source 9 of physiologically compatible solution, such as albumin or HES, so that the physiologically compatible solution d can admix the corpuscle component a1 in a quantity equal to the amount of the plasma combonent b which has been drained.

Reference numeral 10A represents the source of priming fluid, such as normal saline solution, to which the blood outlet H2 is adapted to be connected to link the supply of the physiologically compatible solution d to the blood circulating circuit 1 and the plasma drain passage 200. Reference numeral 10B represents the source of priming solution to which the solution inlet H3 is adapted to be connected for linking the supply of the physiologically compatible solution d to the solution supply passage 300. It is to be noted that these sources 10A and 10B may be combined into a single source such as the source 10 used in the previously described embodiment.

Between a downstream portion of the solution supply passage 300 and a downstream portion of the blood circulating circuit 1 downstream of the plasma filter 3, there is disposed the first valve 11 for selectively establishing and interrupting a fluid circuit therebetween, and the second valve 12 is disposed on the downstream portion of the solution supply passage 300 for selectively establishing and interrupting a fluid circuit between it and the outside of the system.

The plasma filtration apparatus also comprises the first (or blood) and second (or drain) pump drive means 13 and 14, and the pump halting means 15. In response to the application of an external start signal, the first and second valves 11 and 12 are closed and the first pump 4 is driven in a first direction, i.e., driven so as to rotate in a direction counterclockwise as viewed in FIG. 17, so that the priming fluid p can be supplied into the blood circulating circuit 1 so as to flow across the plasma filter 3 in a direction from the lower end to the upper end thereof. The second pump drive means 14, when receiving a detection signal from the first detector 5 indicating that the flow of the priming fluid p through the blood circulating circuit 1 has attained a predetermined value, opens the second valve 12 and drives the second pump 7 so that the priming fluid p can be supplied to the plasma drain passage 200 and the solution supply passage 300. The pump halting means 15 is operable, when detection signals from the first and second detectors 5 and 8 indicate that the flow of the priming fluid p in the blood circulating circuit 1 and that in the plasma circulating circuit 2 have attained a second predetermined value, respectively, to bring the first and second pumps 4 and 7 to a halt, thereby completing the priming operation.

According to the above described construction, as the priming fluid p flows through the plasma filter 3 from the lower end to the upper end thereof, air contained in the plasma filter 3 can be smoothly expelled outside the system through the blood inlet H1. The second pump 7 is held inoperative with no priming fluid supplied in the plasma drain passage 200 before the flow of the priming fluid p supplied into the blood circulating circuit 1 attains the first predtermined value, and therefore, during this period, air contained in the blood circulating circuit 1 can be smoothly expelled to the outside of the system.

Also, the priming fluid p having flowed through the solution supply passage 300 can be discharged to the outside through the drain opening D2 by way of the second valve 121. It will not enter the blood circulating circuit 1 and, therefore, will not contaiminate the blood circulating circuit 1.

Since the priming fluid p flows through the blood circulating circuit 1 and the plasma drain passage 200 until the flow in the blood circulating circuit 1 and that in the plasma drain passage 200 attain the second predetermined value, both can be effectively and satisfactorily cleansed.

The second preferred embodiment of the present invention will now be described. As in the case with the description of the first preferred embodiment, the structure of the blood processing apparatus will first be described.

Figure 18:
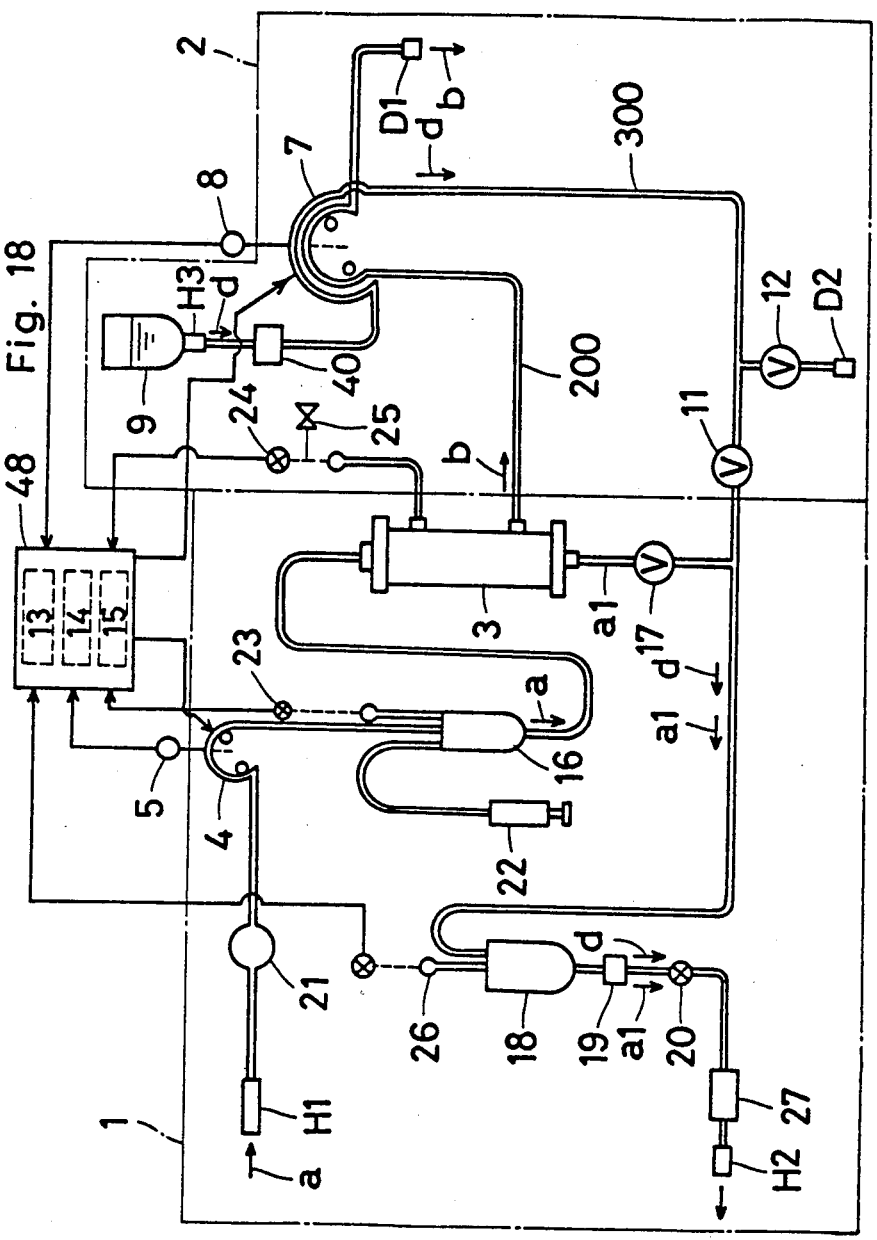
FIG. 18 is a fluid circuit diagram of the plasma filtration apparatus showing a condition in which whole blood is being processed.

Referring to FIG. 18, whole blood a extracted into the blood circulating circuit 1 through the blood inlet H1 which may be a coupler connectable with a shunt, a cannule, a syringe needle or a blood reservoir after the pressure thereof has been increased by the first pump 4, that is, a blood pump, supplied into an arterial pressure chamber 16 and then towards an upper end of the plasma filter 3 which is supported in upright position so as to extend vertically. The whole blood a supplied into the plasma filter 3 from the upper end thereof is separated into the corpuscle component a1 and the plasma component b within the plasma filter 3. The plasma filter 3 may be of any known construction having a semi-permeable, plasma separating membrane, for example, a plate-like, tubular or hollow fiber separating membrane made of a copolymer of polyvinyl alcohol (PVA), it being, however, that the separating membrane comprised of a bundle of hollow fibers is usually employed in the plasma filter 3.

The corpuscle component a1 separated from the whole blood a in the plasma filter 3 is supplied into a venous pressure chamber 18 through a first blood valve 17 and is subsequently supplied through a bubble detector 19 and then through a second blood valve 20 to the blood outlet H2 which may be a coupler connectable with a shunt, a cannule or an instillation unit.

A pillow sensor 21 comprising an expandable bag is disposed upstream of the blood pump 4 with respect to the direction of flow of whole blood towards the plasma filter 3. This pillow sensor 21 is operable in response to a change in blood pressure in the blood flow path in the event that a difficulty arises in blood extraction in such a way that, when it detects the presence of a negative pressure in the blood flow path, the blood pump 4 can be brought to a halt, but when it detects that the negative pressure has been removed, the blood pump 4 once brought to a halt can be restarted. The arterial pressue chamber 16 is connected with a heparine injector 22 for injecting a small quantity of heparine thereinto to mix with the whole blood a thereby avoiding any possible coagulation of the blood being processed, and an arterial pressure sensor 23. The plasma filter 3 is connected with a filtration pressure sensor 24 and an air introducing valve 25. On the other hand, the venous pressue chamber 18 is connected with a venous pressure sensor 26. A blood flow path between the venous pressure chamber 18 and the blood outlet H2 has a bubble detector 27 disposed therein and located in the vicinity of the blood outlet H2.

The plasma component b separated from the whole blood a in the plasma component filter 6 is pumped to the outside of the system by a drain pump 7 through a drain opening D1. On the other hand, the solution inlet H3 is connected through the drain pump 7 and the bubble detector 40 with the source of physiologically compatible solution d from which the physiologically compatible solution d such as albumin or HES can be pumped by the drain pump 7 and then infused to the patient together with the corpuscle component a1 through the downstream portion of the blood circulating circuit 1 downstream of the plasma filter 3. The amount of the physiologically compatible solution d infused to the patient with the corpuscle component a1 is equal to the amount of the plasma component b which has been drained as hereinbefore described.

A fluid path between a downstream portion of the solution supply passage 300 and the downstream portion of the blood circulating circuit 1 downstream of the plasma filter 3 is provided with the first valve 11 for selectively establishing and interrupting the circuit, and a downstream portion of the solution supply passage 300 upstream of the first valve 11 has a branch passage ramified therefrom and provided with the second valve 12 for selectively establishing and interrupting a fluid circuit between the downstream side of the solution supply passage 300 and the outside of the system.

The blood pump 4 and the drain pump 7 are operatively coupled with a blood flow detector 5 and a drain flow detector 8, respectively. The blood flow detector 5 is operable to detect the flow of whole blood a through the blood circulating circuit 1 in terms of the number of revolutions of the blood pump 4. The drain flow detector 8 is operable to detect the flow of the fluid to be drained in terms of the number of revolutions of the drain pump 7.

Flow signals from the detectors 5 and 8 and pressure signals from the pressure sensors 23, 24 and 26 are all fed to a control device 48 comprising a microcomputer which monitors these signals to control, during the clinical use of the apparatus, the respective numer of revolutions of the pumps 4 and 7 for bringing the flow rate in the blood circulating circuit 1, the flow rate in the solution supply passage 300, the flow rate in the plasma drain passage 200 and the membrane pressure in the plasma filter 3 to their respective proper values. While the drain pump 7 is concurrently used to drain the plasma component b to the outside and to supply the physiologically compatible solution d into the solutin supply passage 300, it may be contemplated to use two separate pumps for draining the plasma component b and for supplying the physiologically compatible solution d, respectively. However, the concurrent use of the drain pump 7 for these two purposes such as in the illustrated embodiment of the present invention is advantageous in that, with no need to control the drain pump 7 in two different ways for the respective functions, the amount of the plasma component b to be drained and that of the physiologically compatible solution d supplied can be equalized with each other at all times.

Figure 19:
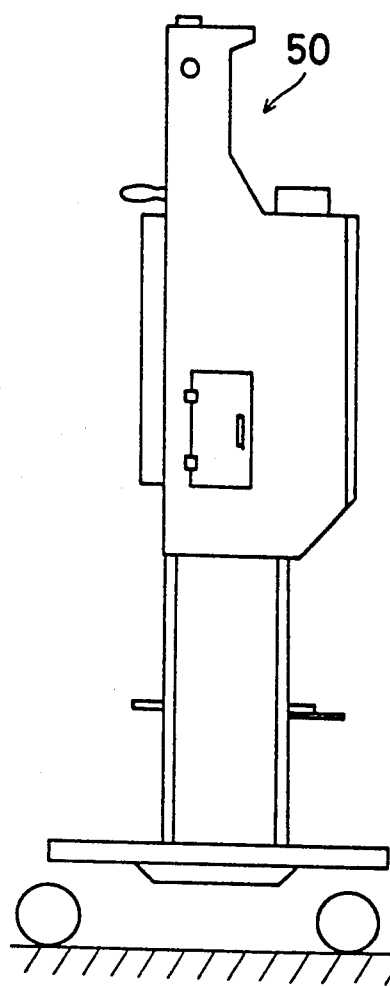
FIGS. 19 and 20 are schematic side and front elevational views of the plasma filtration apparatus.
Figure 20:
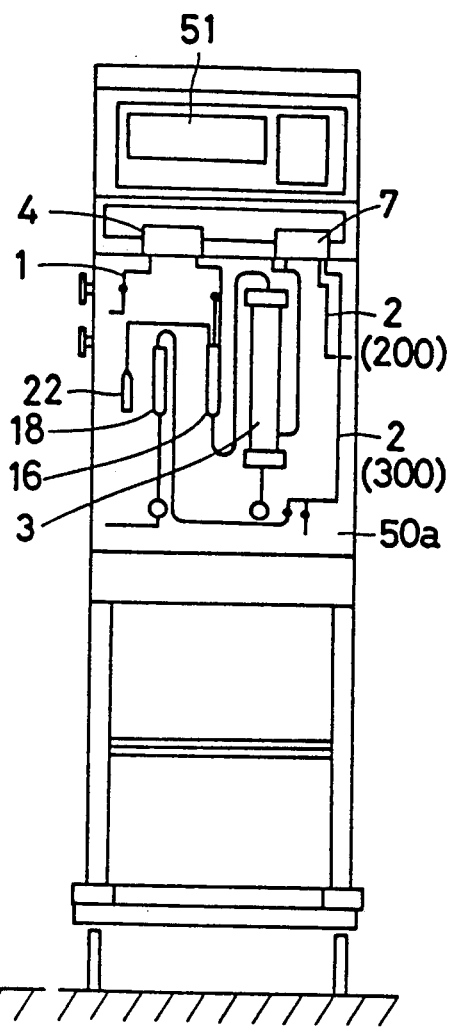

The blood circulating circuit 1, and the plasma circulating circuit 2 including the plasma drain passage 200 and the solution supply passage 300 are installed at a front panel 50a of a caster-equipped console 50 as shown in FIGS. 19 and 20. As best shown in FIG. 20, the front panel 50a of the caster-equipped console 50 has mounted thereon the blood circulating circuit 1 and the plasma circulating circuit 2, each including a corresponding number of tubings made of, for example, polyvinvyl chloride, with the plasma filter 3 and the other component parts being interposed therein. At the top of the caster-equipped console 50, there is disposed a control panel having various control knobs for issuing commands necessary to control the blood pump 4 and the drain pump 7, which control panel also includes a display unit 51 for displaying data being monitored and a description representative of the sequence of manipulations to be carried out.

The priming operation to be carried out using the blood processing apparatus of the construction described hereinabove with reference to FIGS. 18 to 20 will now be described.

Figure 21:
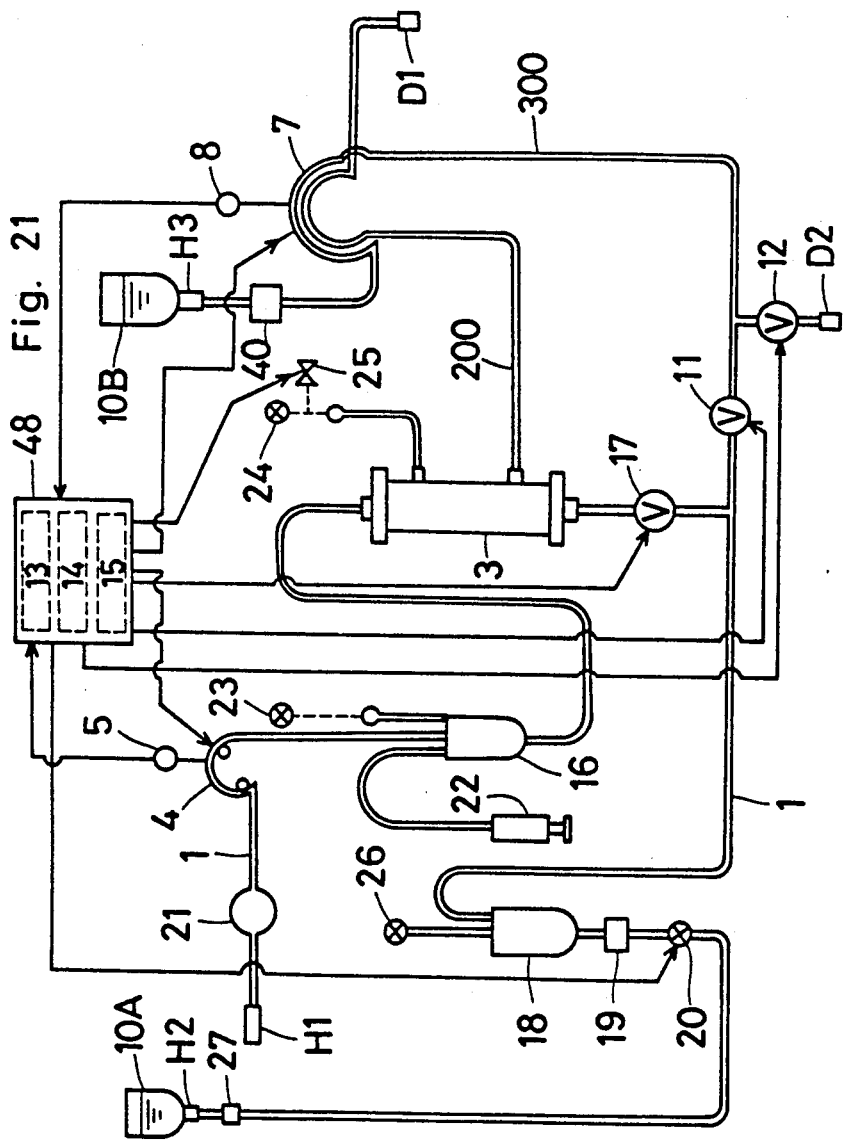
FIG. 21 is a fluid circuit diagram of the plasma filtration apparatus according to the second preferred embodiment of the present invention.

Referring to FIG. 21, the blood outlet H2 is fluid-connected through the bubble detector 27 with a source 10A of priming solution, i.e., normal saline solution, and the solution inlet H3 upstream of the bubble detector 40 is fluid-connected with the priming solution source 10B in place of the physiologically compatible solution source 9 (FIG. 18). The control device 48 has built therein a first pump drive means 13 for driving the blood pump 4, a second pump drive means 14 for driving the drain pump 7, and a pump halting means 15.

Figure 22:
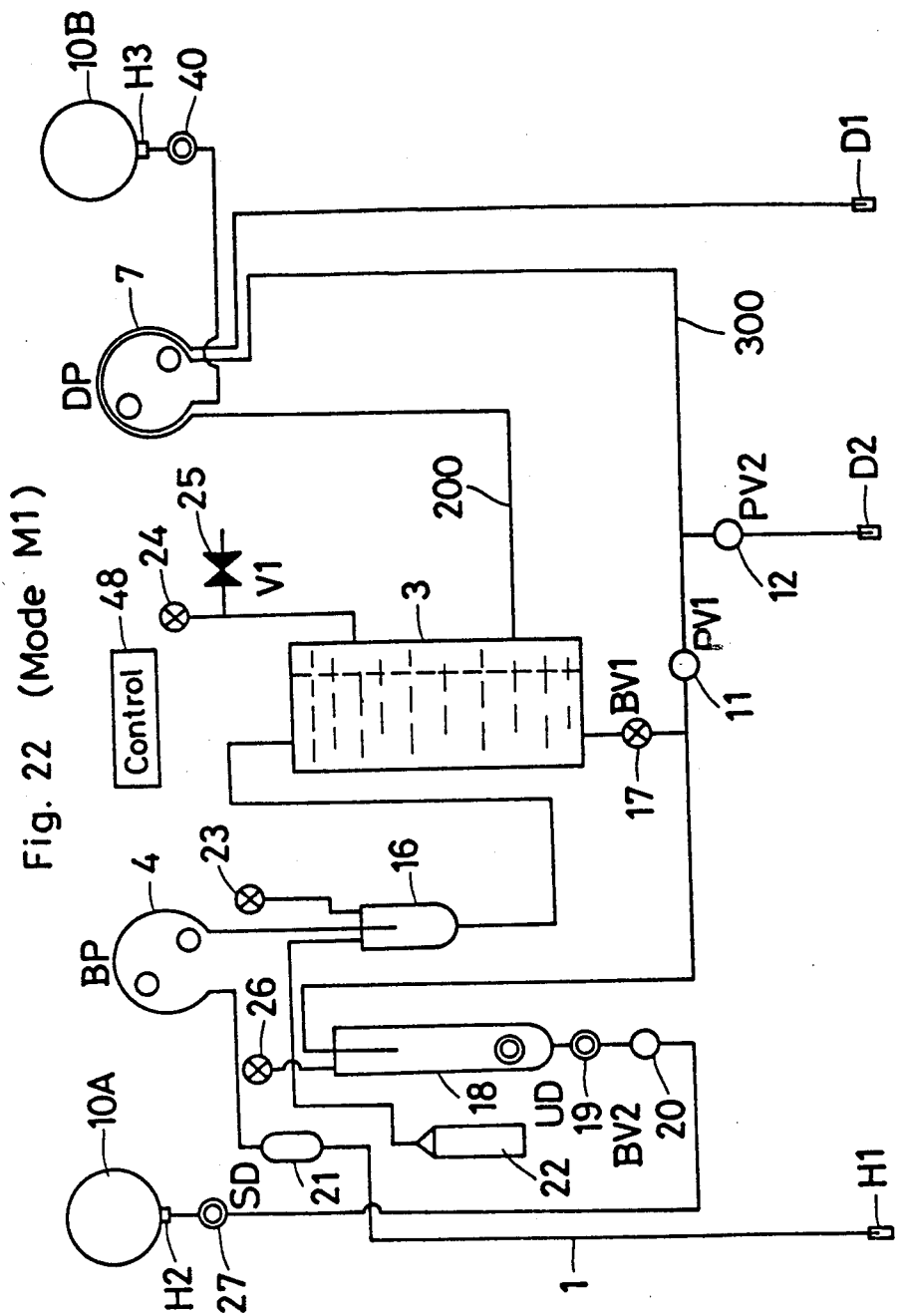
FIGS. 22 to 27 are schematic fluid circuit diagrams showing the sequence of operation of the plasma filtration apparatus according to the second preferred embodiment.

On the other hand, since the plasma filter 3 is normally filled with normal saline solution or distilled water, the first blood valve 17 is, at the outset of the priming operation, closed to enable the plasma filter 3 to be set in position withe no possibility of the solution or water leaking out from the plasma filter 3, thereby avoiding any possible entry of air into the plasma filter 3. This condition of the system is shown in FIG. 22 and is hereinafter referred to as Mode M1 ready for the actual use of the apparatus for the priming operation.

Figure 23:
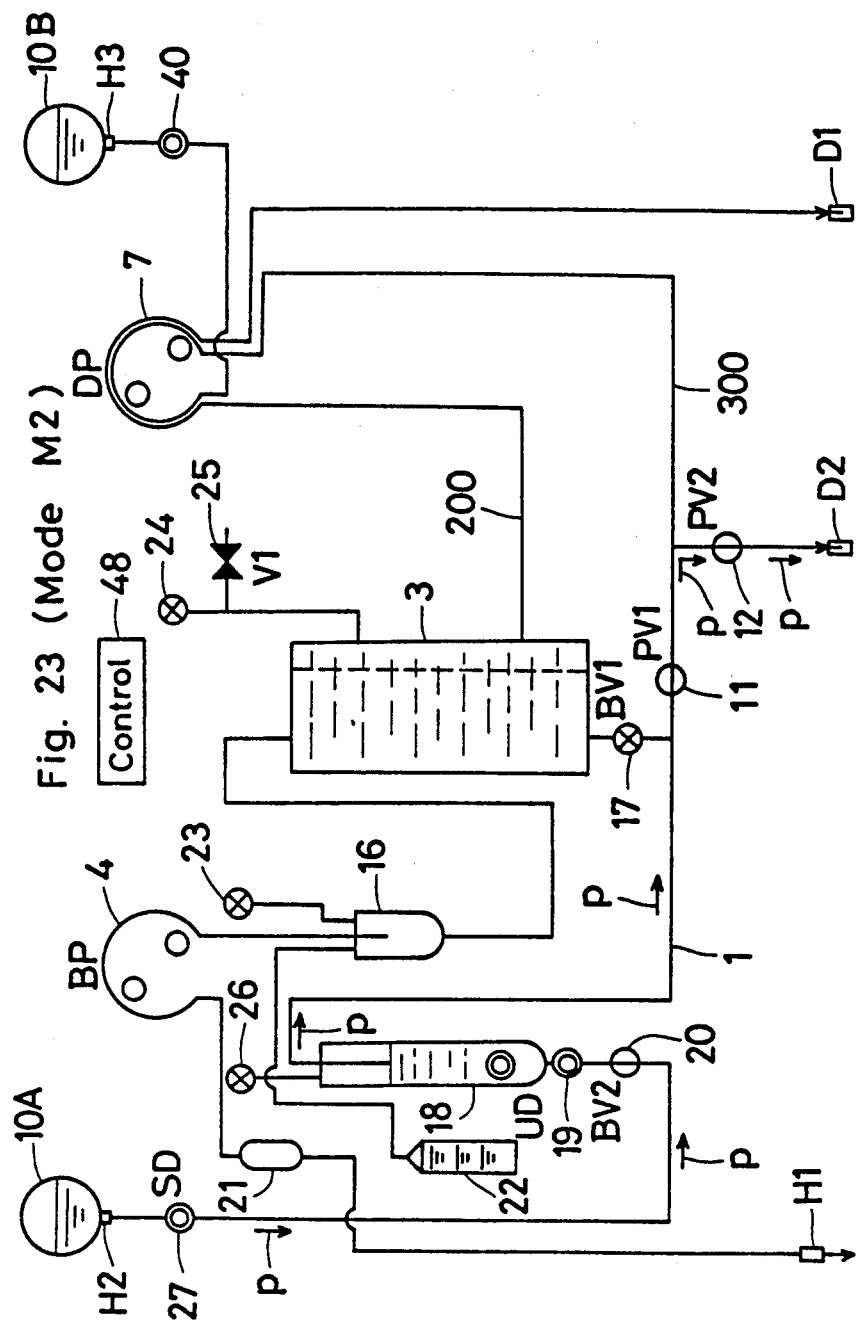

The sequence of the priming operation carried out using the apparatus is shown in FIGS. 23 to 27, reference to which will now be made. FIG. 23 illustrates another condition of the system referred to as Mode M2 in which, while all of the pumps 4 and 7 are held inoperative, the control device 48 is activated in response to an external start signal, applied thereto, to close the air introducing valve 25 and, on the other hand, to open the first valve 11, the second valve 12 and the second blood valve 20. As a result thereof, the priming solution p flows from the priming solution source 10A to the outside of the system through the second blood valve 20, the bubble detector 19, the venous pressure chamber 18, the first valve 11, and the second valve 12 and finally through the drain opening D2 in the order specified above with the consequence that air contained in a portion of the blood circulating circuit 100 on the side of the blood outlet H2 can be expelled to the outside of the system.

Figure 24:
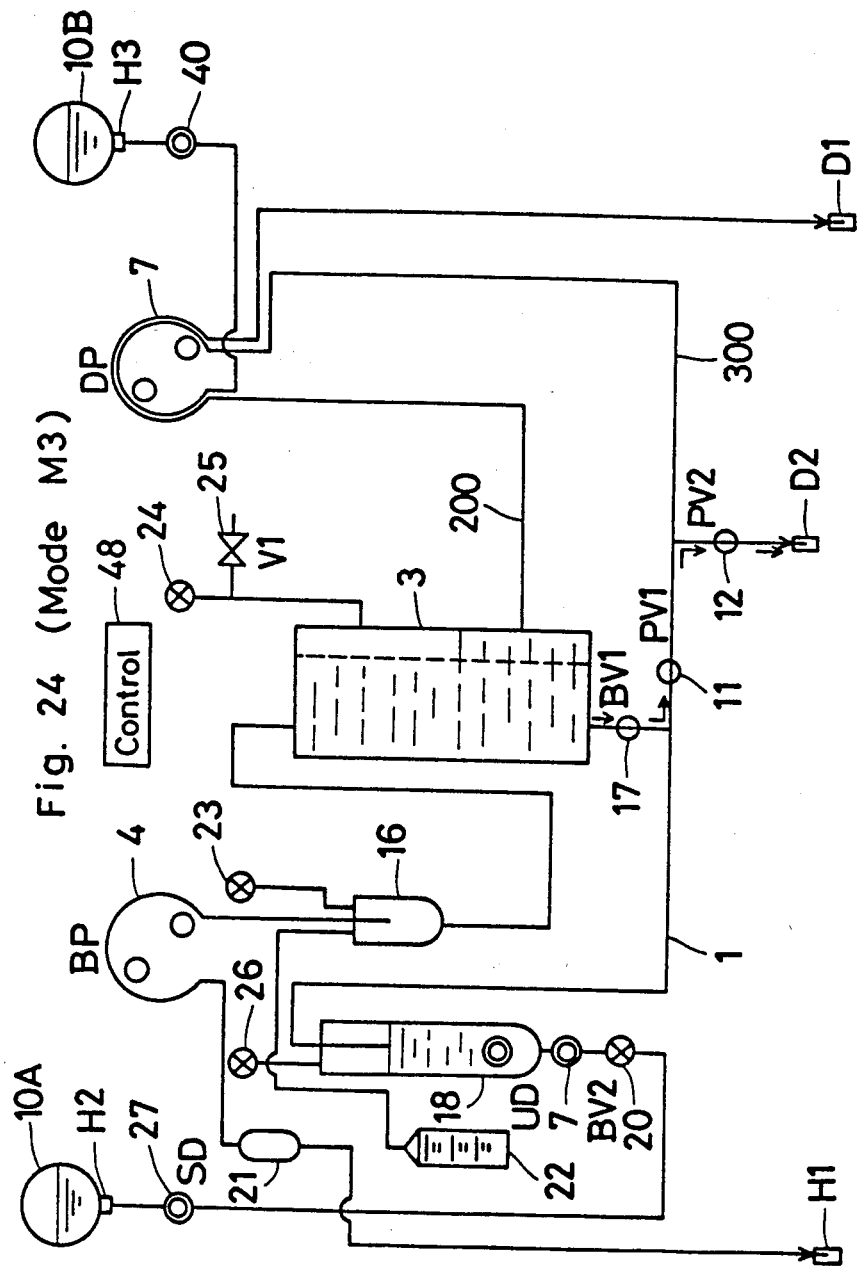

During the subsequent condition shown in FIG. 24 and referred to as Mode M3, the second blood valve 20 and both the air introducing valve 25 and the first blood valve 17 are closed and opened, respectively, in response to associated command signals generated from the control device 48. Although it seems that the opening of the air introducing valve 25 permits the entry of air therethrough towards the plasma filter 3, no air will in actuality enter the hollow interior of the plasma filter 3. Therefore, during Mode M3 shown in FIG. 8, only the solution within a plasma chamber of the plasma filter 3 is allowed to permeate into the hollow fibers and is subsequently discharged to the outside through the drain opening D2 by way of the first blood valve 17, then, the first valve 11 and, finally, the second valve 12.

Figure 25:
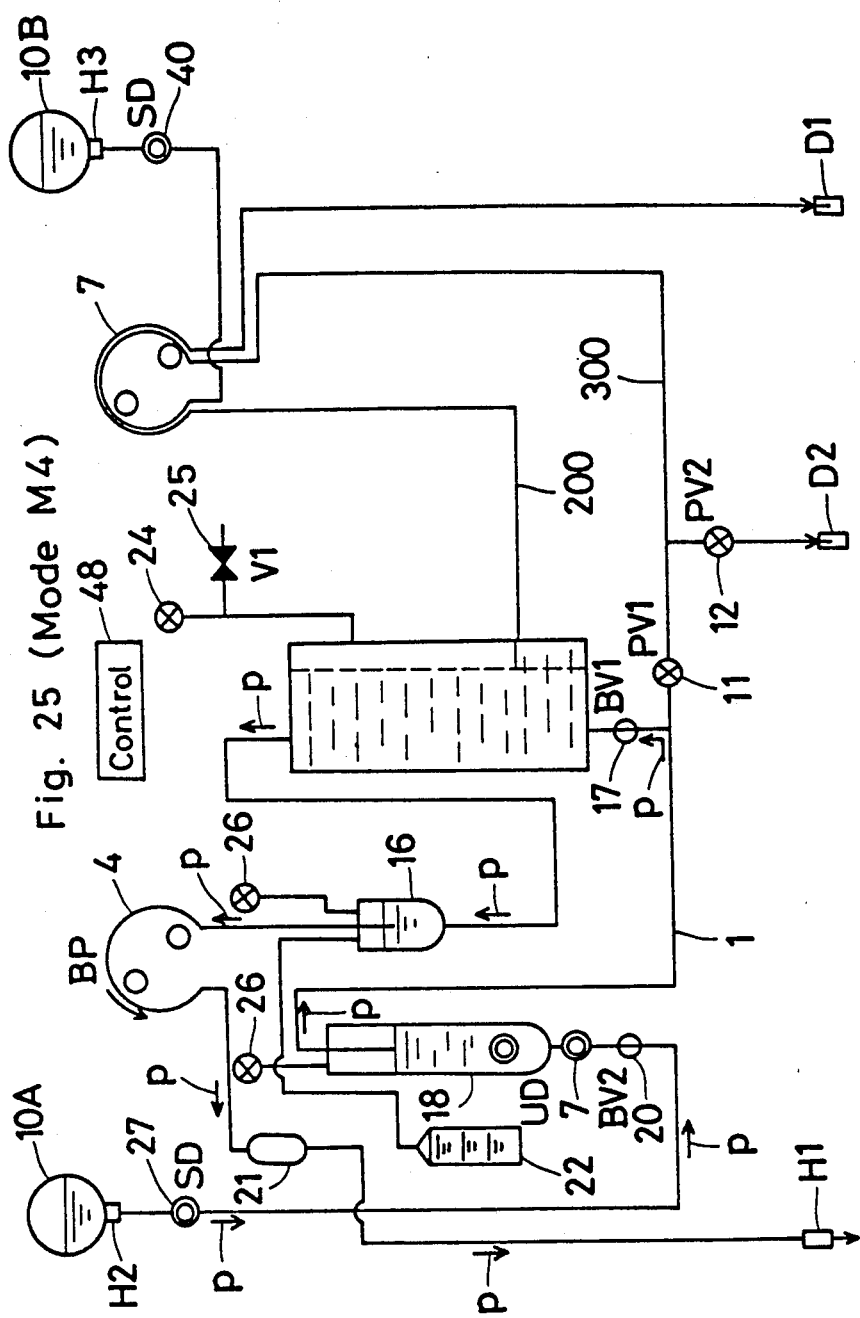

During Mode M4 shown in FIG. 25, the control device 48 causes the second blood valve 20 and the first blood valve 17 to open and the air introducing valve 25 and the first and second valves 11 and 12 to close and also causes the blood pump 4 to reverse its direction of rotation so that the priming solution p can flow through the entire blood circulating circuit 1 for cleansing the fluid circuit components and also for expelling air contained therein. Since at this time the priming solution p flows across the plasma filter 3 in a direction from the lower end to the upper end thereof, air contained in the plasma filter 3 can be smoothly expelled out of the plasma filter 3 and then discharged to the outside through the arterial pressure chamber 16, the blood pump 4, the pillow sensor 21 and finally the blood inlet H1.

Figure 26:
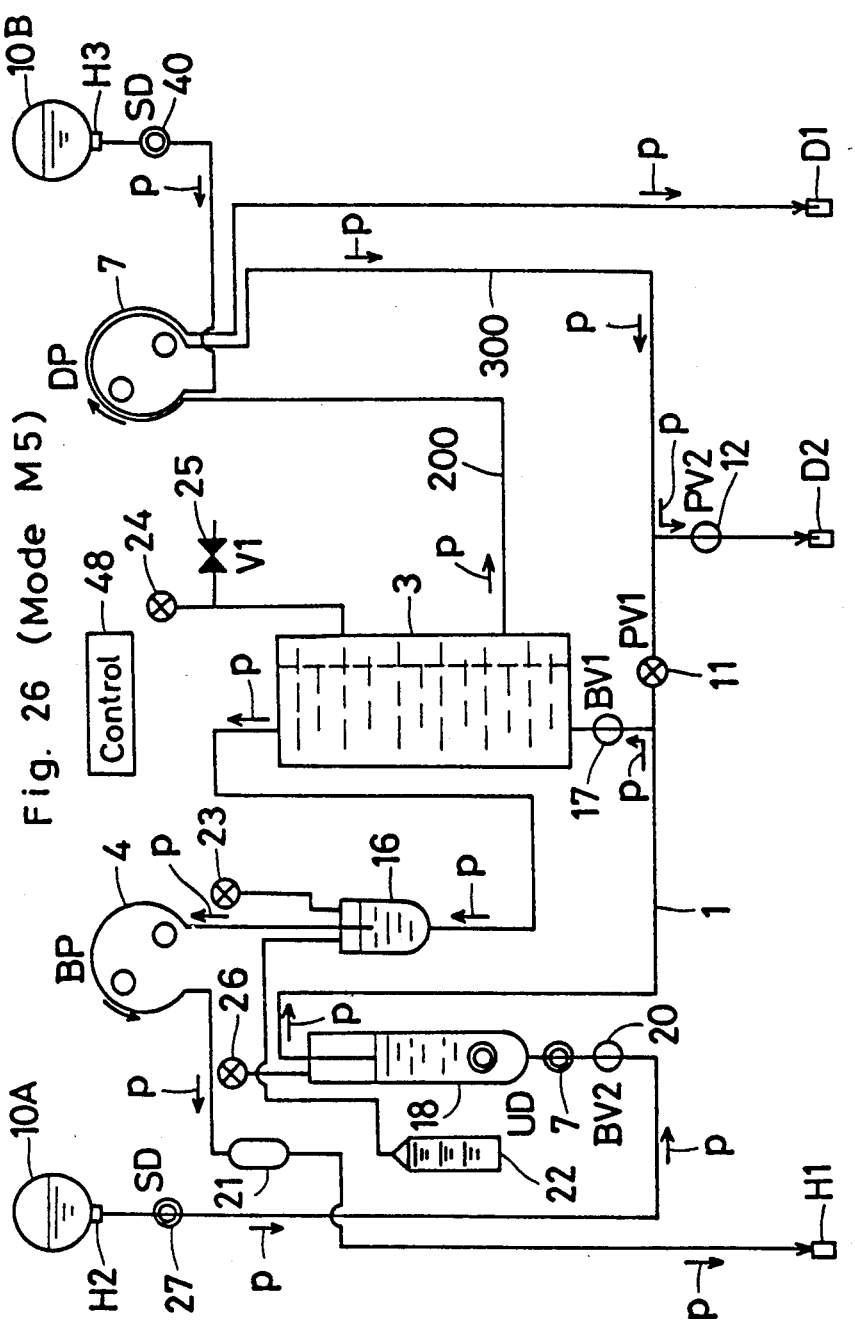
Figure 27:
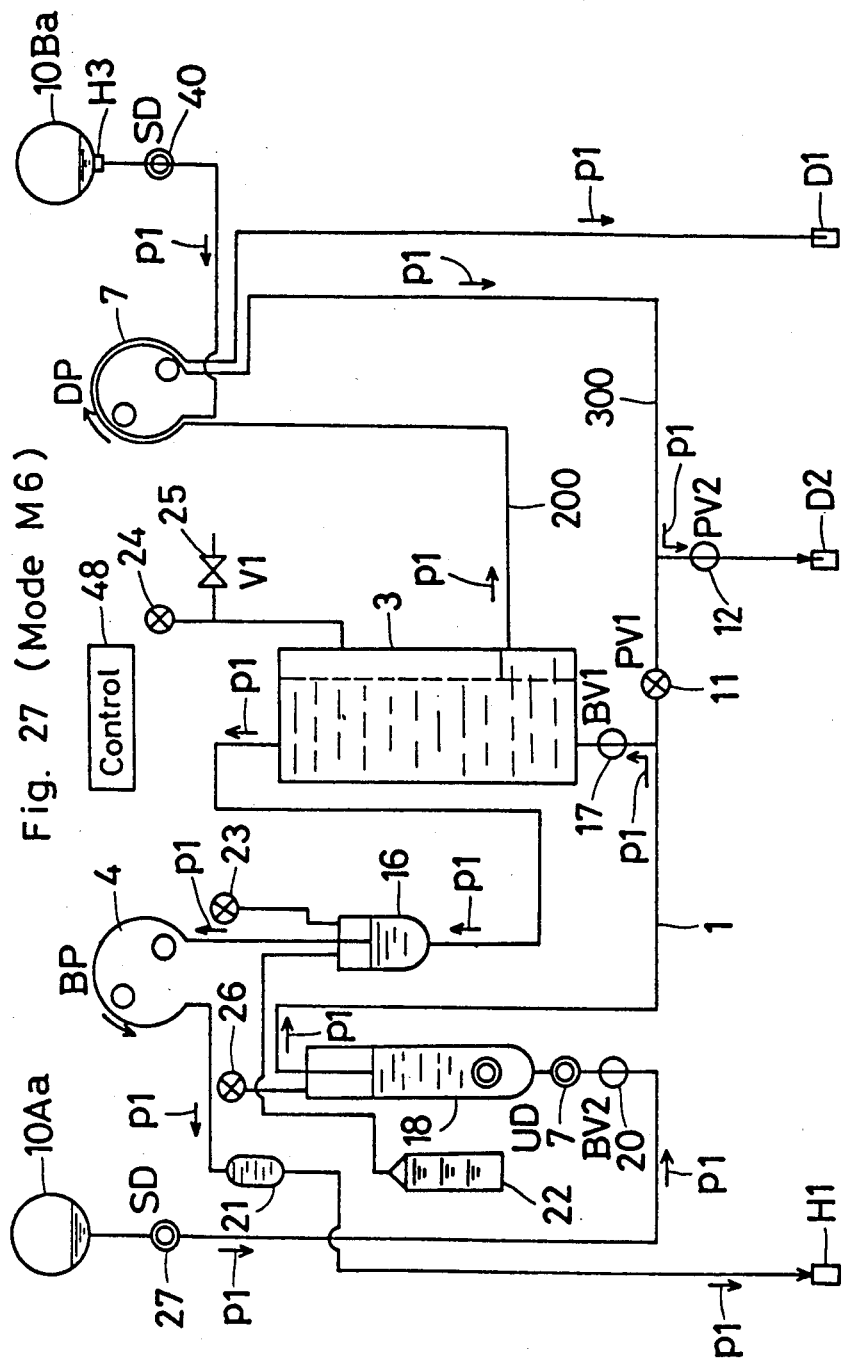

When the flow output generated from the blood flow detector 5 (FIG. 21) applied to the control device 48 indicates that the flow rate in the blood circulating circuit 1 has attained a first predetermined value, this means that air in the blood circulating circuit 1 has been completely expelled to the outside of the system and, therefore, Mode M5 shown in FIG. 26 takes place. As shown in FIG. 26, during Mode M5, the control device 48 generates commands necessary to drive the drain pump 7 in a first direction required to permit a portion of the priming solution supplied to the plasma filter 3 second penetrate across the membrane and then to be discharged to the outside through the drain opening D1. Also, the priming solution p supplied to the solution supply passage 300 by the operation of the drain pump 7 is discharged to the outside through the drain opening D2 by way of the second valve 12. In this condition, the apparatus undergoes a normal operation with the priming solution p being supplied through the plasma drain passage 200 and the solution supply passage 300 to perform both the cleansing of and the removal of air from the plasma drain passage 200 and the solution supply passage 300. Since at this time the priming solution p, contaminated as a result of the flow thereof through the solution supply circuit 300, can be discharged to the outside through the drain opening D2 by way of the second valve 12. It will not enter the blood circulating circuit 1 and, therefore, there is no possibility that the blood circulating circuit 1 may be contaminated.

When intelligence derived from the respective output signals from the blood flow detector 5 and the plasma flow and drain flow detector 8 indicates that the flow rate in the blood circulating circuit 1, the flow rate in the plasma drain passage 200 and the flow rate in the solution supply passage 300 have attained a predetermined value, the control device 48 causes the display unit 51 (FIG. 20) to display an indication that the priming with the priming solution mixed with heparin should be carried out, while triggering a warning device, for example, a chime, to call the attention of an operator of the apparatus. The operator then acts, in response to the visual indication displayed in the display unit 51 and/or the audio indication issued by the warning device, to disconnect the priming solution sources 10A and 10B and to connect sources 10A$a$ and 10B$a$ of priming solution p1 mixed with heparin, this condition being shown in FIG. 27 and referred to as Mode M6. Thereafter, the normal operation is continued. It is to be noted that for the purpose of the subsequent description the priming solution p1 mixed with the heparin which is supplied from the priming solution sources 10A$a$ and 10B$a$ is hereinafter referred to as "mixed priming solution".

When the output signals from the blood flow detector 5 and the plasma flow and drain flow detector 8 applied thereto indicate that the cumulative flow of the priming solution p and the mixed priming solution p1 both having flowed through the blood circulating circuit 1 and both the plasma drain passage 200 and the solution supply passage 300 have attained a second predetermined value, the control device 48 determines that the cleansing of and the removal or air from the blood circulating circuit 1, the plasma drain passage 200 and the solution supply passage 300 have finished, and brings all of the pumps 4 and 7 to a halt, thereby completing the priming cycle.

Hereinafter, the priming cycle executed by the control device 48 will be described with reference to the flow charts shown in FIGS. 28 and 29. Before the desciption proceeds, the following abbreviations used in the flowcharts are used to denote the following respective component parts of the apparatus.

PV1 stands for the first valve 11; PV2 for the second valve 12; BV1 for the first blood valve 17; BV2 for the second blood valve 20; V1 for the air introducing valve 25; UD for the veous pressure chamber 18; SD for the bubble detector 27; BP for the blood pump 4; and DP for the drain pump 7.

Figure 28:
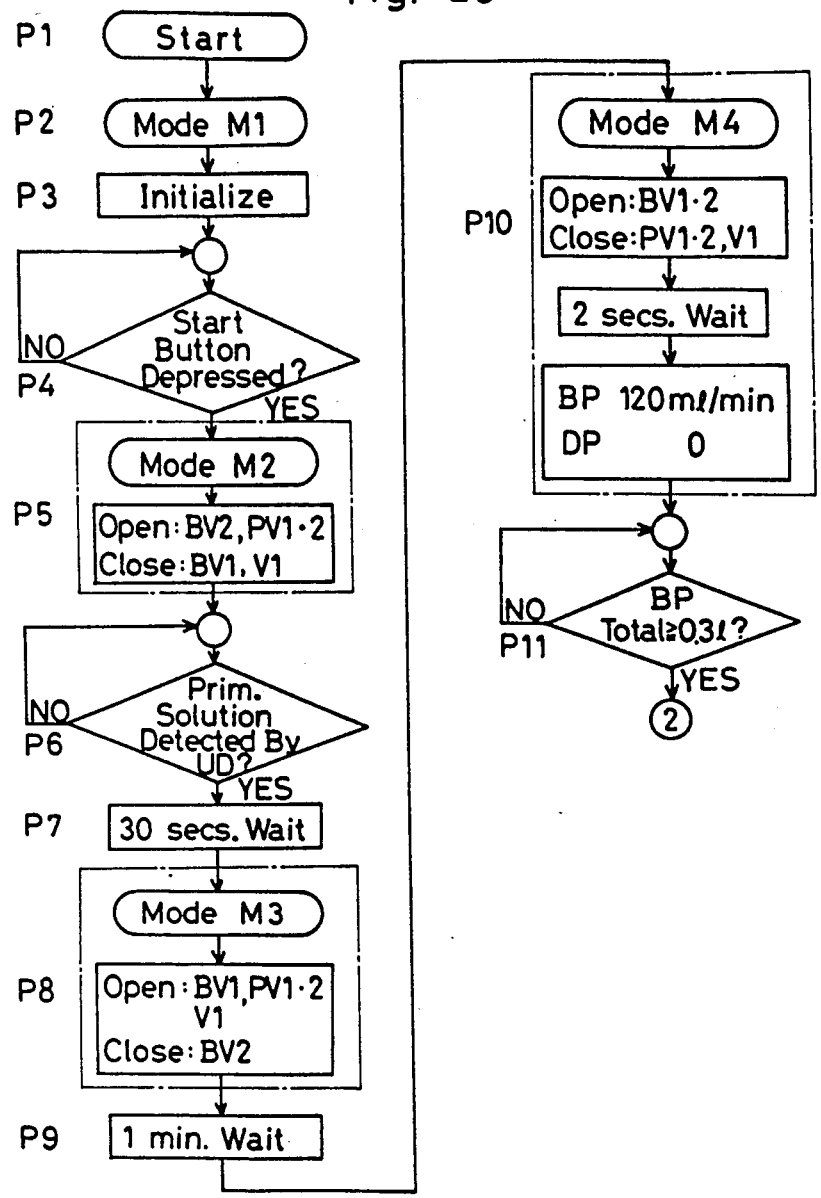
FIGS. 28 and 29 are flow charts showing the method of controlling the plasma filtration apparatus according to the second preferred embodiment.
Figure 29:
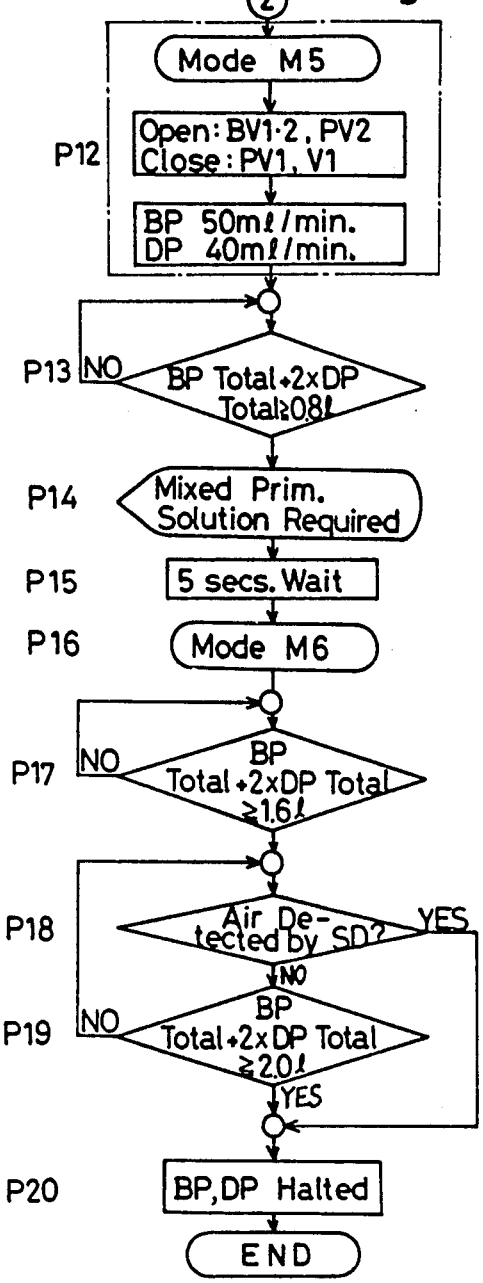

Referring first to FIG. 28 and subsequent to the start at step P1, Mode M1 (FIG. 22) takes place at step P2 in readiness for the actual priming cycle. After the initialization at step P3, a decision is made at step P4 to determined if a start button (not shown) has been depressed. If the start button has been depressed, the program flow proceeds to step P5 at which Mode M2 (FIG. 23) takes place. As hereinbefore described, during Mode S2, BV2, PV1 and PV2 are all opened and BV1 and V1 are closed so that the air contained in the downstream portion of the blood circulating circuit 1 can be expelled to the outside.

Subsequently, step P6 is executed at which a decision is made to determine if UD has detected the level of the priming solution. When and after UD has detected the level of the priming solution, the control device 48 waits for, for example, 30 seconds at step P7, which time is required to complete the total removal of air from the blood circulating circuit 1.

The program flow then proceeds to step P8 at which Mode M3 (FIG. 24) takes place. During this Mode M3, BV1, PV1, PV2 and V1 are all opened and BV2 is closed as hereinbefore described, so that the distilled water remaining within the plasma component filter 3 is removed. The removal of the distilled water continues for, for example, one minute at step P9.

Thereafter, step P10 is executed at which Mode M4 (FIG. 25) takes place. As hereinabove described, during Mode M4, BV1 and BV2 are opened, PV1, PV2 and V1 are all closed and BP is reversed, i.e., driven in a second direction opposite to the first direction, so as to attain the discharge rate of, for example, 120 ml per minute to effect the supply of the priming solution p throughout the blood circulating circuit 1. At step P11, a decision is made to determine if the cumulative discharge amount of BP, that is, the cumulative flow rate in the blood circulating circuit 1, has exceeded a first predetermined value, for example, 0.3 ml. In the event that the result of the decision at step P11 indicates that the cumulative flow rate in the blood circulating circuit 1 has exceeded the first predetermined value, it means that the air in the blood circulating circuit 1 has been completely removed, and therefore, the program flow proceeds to step P12 shown in FIG. 29, during which step P12 Mode M5 (FIG. 26) takes place. As hereinbefore described, during this Mode M5, BV1, BV2 and PV2 are opened, PV1 and V1 are closed, BP is driven in a second direction reverse to the first direction so as to discharge at a rate of, for example, 50 ml per minute and DP is driven in the first direction so as to discharge at a rate of, for example, 40 ml per minute, thereby to supply the priming solution p to the plasma drain passage 200 and the solution supply passage 300.

Thereafter, when the cumulative flow represented by the discharge amount from BP plus twice the discharge amount from DP has been detected at step P13 as exceeding a predetermined value, for example, 0.8 ml, both the removal of air and the cleansing with the use of the priming solution p are deemed finished, with the program flow consequently proceeding to step P14.

At step P14, the visual indication that the mixed priming solution source should be connected is displayed on the display unit 51 and, at the same time, the chime is rung to this effect to call the attention of the operator. When the operator connects the mixed priming solution source, the chime is turned off and a period of about 15 seconds is waited for at subsequent step P15, followed by step P16 during which Mode M8 (FIG. 27) takes place to continue the normal operation as during Mode M7.

Thereafter, and when the cumulative flow represented by the discharge amount from BP plus twice the discharge amount from DP has been detected at step P17 as attaining a value greater than, for example, 1.6 ml, it means that the amount of the priming solution contained in the priming solution source is small and, therefore, SD is brought, at step P18, in position ready to detect the air. If no air is dtected by SD, the program flow proceeds to step P19 and, in the event that the cumulative flow referred to above is detected as exceeding a second predetermined value, for example, 2.0 ml, step P19 is followed by step P20 to bring BP and DP to a halt, thereby completing the priming cycle at step P21. On the other hand, if the air is detected by CD at step P18, it means that the whole amount of the priming solution has been consumed, and therefore, the program flow proceeds to step P20.

Although the present invention has been fully described in connection with the preferred embodiments with reference to the accompanying drawings, it is to be noted that various changes and modifications will be apparent to those skilled in the art without departing from the scope of the present invention as defined by the appended claims. Although in the foregoing embodiments the plasma filter 3 is used in the form of a so-called wet-type wherein normal saline solution or distilled water is filled therein during the manufacture thereof, the plasma filter having not yet been filled with any liquid medium, that is, the so-called dry-type, may be employed in the practice of the present invention. In such case, Mode S3 in the case of the first preferred embodiment, or Mode M3 in the case of the second preferred embodiment, executed for the purpose of removing the liquid medium contained in the plasma filter 3 could be obviated.

Therefore, such changes and modifications are to be construed as encompassed within the scope of the present invention.

What is claimed is:

1. A plasma filtration apparatus which comprises:
    a blood circulating circuit means including a plasma filter for separating whole blood, extracted from a subject of interest through a blood inlet, into a blood plasma component and a blood corpuscle component and for supplying the blood corpuscle component to a blood outlet for the return thereof to the subject of interest;
    a plasma circulating circuit means for draining at least a portion of the blood plasma component, which has been separated from the whole blood, and for supplying a physiologically compatible fluid substitute in a quantity substantially equal to the amount of said portion of the blood plasma component, which has been drained, to a portion of the blood circulating circuit means downstream of the plasma filter and then to the blood outlet;
    a first pumping means disposed on the blood circulating circuit means;
    a second pumping means disposed on the plasma circulating circuit means;
    a source of priming fluid adapted to be fluid-connected with the blood outlet and a fluid intake for receiving the fluid substitute into the plasma circulating circuit means;
    a first detector for detecting the flow through the blood circulating circuit means;
    a second detector for detecting the flow through the plasma circulating circuit means;
    a first valve means for selectively establishing and interrupting a first fluid circuit between a downstream portion of the plasma circulating circuit means adjacent the blood outlet and said portion of the blood circulating circuit means downstream of the plasma filter;
    a second valving means for selectively establishing and interrupting a second fluid circuit between said portion of the plasma circulating circuit means adjacent the blood outlet and the outside of the apparatus;
    a first drive means operable to cause the first and second valving means to interrupt the respective first and second fluid circuits and for driving the first pumping means to cause the priming fluid to flow through the blood circulating circuit means;
    a second drive means operable in response to an output signal from the first detector for causing the second valving means to establish the second fluid circuit and, at the same time, driving the second pumping means to cause the priming fluid to flow through the plasma circulating circuit means when the flow through the blood circulating circuit means attains a first predetermined value; and
    means operable in response to respective output signals from the first and second detectors for bringing the first and second pumping means to a halt when both of the flows through the blood circulating circuit means and the plasma circulating circuit means attain a second predetermined value.

2. The apparatus as claimed in claim 1, wherein the plasma circulating circuit means has a plasma component filter for separating the plasma component into a high molecular component to be drained and a low molecular component to be returned to the subject of interest.

3. The apparatus as claimed in claim 2, wherein the plasma filter has a plasma inlet port and a corpuscle outlet port and is supported in upright position with the plasma inlet and corpuscle outlet ports oriented upwards and downards, respectively, and the plasma component filter also has a component inlet port and a component outlet port and is supported in upright position with the component inlet and outlet ports oriented downwards and upwards, respectively.

4. The apparatus as claim in claim 1, wherein the plasma circulating means has a plasma drain passage for draining the blood plasma component, which has been separated from the whole blood, and a fluid supply passage for supplying a physiologically compatible fluid substitute in a quantity substantially equal to the amount of the blood plasma component, which has been drained, to a portion of the blood circulating circuit means downstream of the plasma filter and then to the blood outlet.

5. The apparatus as claimed in claim 4, wherein the plasma filter has a plasma inlet port and a corpuscle outlet port and is supported in upright position with the plasma inlet and corpuscle outlet ports oriented upwards and downwards.

* * * * *